United States Patent [19]

Cho et al.

[11] Patent Number: 4,980,552
[45] Date of Patent: Dec. 25, 1990

[54] HIGH RESOLUTION PET SCANNER USING ROTATING RING ARRAY OF ENLARGED DETECTORS HAVING SUCCESSIVELY OFFSET COLLIMATION APERTURES

[75] Inventors: Zang-Hee Cho, Corona Del Mar; Monte S. Buchsbaum; William E. Bunny, both of Laguna Beach; Richard M. Friedenberg, Santa Ana; Edward K. Wong, Jr., Newport Beach, all of Calif.

[73] Assignee: The Regents of the University of California, Oakland, Calif.

[21] Appl. No.: 368,707

[22] Filed: Jun. 20, 1989

[51] Int. Cl.⁵ .................... G01T 1/164; G01T 1/20
[52] U.S. Cl. .................... 250/363.03; 250/363.02; 250/363.04; 250/363.10; 250/366; 250/505.1
[58] Field of Search .............. 250/363.03, 363.02, 250/363.04, 363.10, 366, 505.1

[56] References Cited

U.S. PATENT DOCUMENTS

| | | | |
|---|---|---|---|
| 3,585,387 | 6/1971 | Bramlet | 250/363.01 |
| 4,295,047 | 10/1981 | Koga et al. | 250/363.04 |
| 4,309,611 | 1/1982 | Tanaka et al. | 250/363.03 |
| 4,352,018 | 9/1982 | Tanaka et al. | 250/363.03 |
| 4,389,569 | 6/1983 | Hattori et al. | 250/363.04 |
| 4,473,749 | 9/1984 | Derenzo et al. | 250/363.04 |
| 4,514,632 | 4/1985 | Barrett | 250/368 |
| 4,531,058 | 7/1985 | Burnham et al. | 250/363.03 |
| 4,584,478 | 4/1986 | Genna et al. | 250/363.04 |
| 4,733,083 | 3/1988 | Wong | 250/363.03 |
| 4,743,764 | 5/1988 | Casey et al. | 250/363.03 |
| 4,748,328 | 5/1988 | Cahng et al. | 250/363.04 |
| 4,749,863 | 6/1988 | Casey et al. | 250/363.03 |
| 4,774,410 | 9/1988 | Hsieh | 250/363.10 |
| 4,782,233 | 11/1988 | Genna et al. | 250/363.10 |

FOREIGN PATENT DOCUMENTS

58-55876  4/1983  Japan .............................. 250/363.04

OTHER PUBLICATIONS

K. Ishii, S. Watanuki, H. Orihara, M. Itoh and T. Matsuzawa, "Improvement of Time Resolution in a TOF PET System With the Use of BaF₂ Crystals", *Nuclear Instruments and Methods in Physics Research*, vol. A253 (Dec. 15, 1986), pp. 128–134; Copyright ©Elsevier Science Publishers B.V.

Z. H. Cho, K. S. Hong, J. B. Ra, S. Y. Lee, S. K. Hilal and J. Correll, "A New Sampling Scheme for the Ring Positron Camera: Dichotomic Ring Sampling", *IEEE Transactions on Nuclear Science*, vol. 28, No. 1 (Feb. 1981), pp. 94–98; Copyright ©1981 IEEEs.

Cho et al., "High—Resolution Circular Ring Positron Tomograph with Dichotomic Sampling: Dichotom—I", *Phys. Med. Biol.*, vol. 8, No. 11, pp. 1219–1234, 1983.

Tanaka, "Recent Progress on Single Photon and Positron Emission Tomography—From Detectors to Algorithms", *IEEE Transactions on Nuclear Science*, vol. NS—34, No. 1, pp. 313–320, Feb. 1987.

(List continued on next page.)

*Primary Examiner*—Constantine Hannaher
*Attorney, Agent, or Firm*—Nixon & Vanderhye

[57] ABSTRACT

A greatly reduced number of scintillation cyrstal/PMT gamma ray detectors are employed in a ring array about a PET image volume. Because of the relatively small number of such detectors, the complexity and expense of associated electronic signal processing channels is greatly reduced (even if each such channel is provided with sophisticated time of flight capabilities). Similarly, because relatively fewer crystals are employed, it becomes possible to use much larger and faster response time scintillation crystals so as to greatly increase gamma ray detection efficiency and scatter rejection while also permitting the electronic circuits to better reject random events and to provide effective time of flight image data filtering. By providing successively offset collimation apertures for each successive detector of the ring array and by rotating the array 360 degrees through a large number of successive view angle positions, it is nevertheless possible to acquire extremely high resolution image data with a greatly reduced system cost. A multiple aperture embodiment provides improved sensitivity by using associated light collimators and photodiodes in conjunction with slow coincidence steering circuits.

41 Claims, 24 Drawing Sheets

OTHER PUBLICATIONS

Genna et al., "The Development of Aspect, An Annular Single Crystal Brain Camera For High Efficiency Spect", *IEEE Transactions on Nuclear Science*, vol. 35, No. 1, pp. 654–658, Feb. 1988.

Rogers et al., "Conceptual Design of A Whole Body PET Machine", *IEEE Transactions On Nuclear Science*, vol. 35, No. 1, pp. 680–684, Feb. 1988.

Muehllehner et al., "Design and Performance of A New Positron Tomograph", *IEEE Transactions On Nuclear Science*, vol. 35, No. 1, pp. 670–674, Feb. 1988.

Derenzo et al., "A Positron Tomograph With 600 BGO Crystals and 2.6 MM Resolution", *IEEE Transactions On Nuclear Science*, vol. 35, No. 1, pp. 659–664, Feb. 1987.

Dorenzo et al., "Initial Results From the Donner 600 Crystal Positron Tomograph", *IEEE Transactions On Nuclear Science*, vol. NS—34, No. 1, pp. 321–325, Feb. 1987.

Muehllehner et al., "Advances in SPECT and PET", *IEEE Transactions On Nuclear Science*, vol. 35, No. 1, pp. 639–643, Feb. 1988.

Lewellen et al., "Performance Measurements of the SP3000/UW Time—of—Flight Positron Emission Tomograph", *IEEE Transactions On Nuclear Science*, vol. 35, No. 1, pp. 665–667, Feb. 1988.

Burnham et al., "Cylindrical PET Detector Design", *IEEE Transactions On Nuclear Science*, vol. 35, No. 1, pp. 675–679, Feb. 1988.

Carrier et al., "Design of A High Resolution Positron Emission Tomograph Using Solid State Scintillation Detectors", *IEEE Transitions On Nuclear Science*, vol. 35, No. 1, pp. 685–690, Feb. 1988.

Bice et al., "Simplified Detection System For Neuroreceptor Studies In the Human Brain", *The Journal of Nuclear Medicine*, vol. 27, No. 2, pp. 184–191, Feb. 1986.

OFFSET OF COLLIMATOR APERTURE CENTER FROM CENTER OF DETECTOR

FIG. 15A

| GANTRY POSITION 1 | | | | | | | | | | | | | | | | | | | | | | | |
|---|---|---|---|---|---|---|---|---|---|---|---|---|---|---|---|---|---|---|---|---|---|---|---|
| DETECTOR i | 1 | 1 | 2 | 2 | 3 | 3 | 4 | 4 | 5 | 5 | 6 | 6 | 7 | 7 | 8 | 8 | 9 | 9 | 10 | 10 | 11 | 11 | 12 |
| DETECTOR j | 12 | 13 | 13 | 14 | 14 | 15 | 15 | 16 | 16 | 17 | 17 | 18 | 18 | 19 | 19 | 20 | 20 | 21 | 21 | 22 | 22 | 23 | 23 |
| REBINNED TO BIN GROUP | R1 | L1 | R3 | L3 | R5 | L5 | R7 | L7 | R9 | L9 | R11 | L11 | R13 | L13 | R15 | L15 | R17 | L17 | R19 | L19 | R21 | L21 | R23 |
| RAY NUMBER IN BIN | n/a | 1 | 1 | 2 | 2 | 3 | 3 | 4 | 4 | 5 | 5 | 6 | 6 | 7 | 7 | 8 | 8 | 9 | 9 | 10 | 10 | 11 | 11 |

| GANTRY POSITION 2 | | | | | | | | | | | | | | | | | | | | | | | |
|---|---|---|---|---|---|---|---|---|---|---|---|---|---|---|---|---|---|---|---|---|---|---|---|
| DETECTOR i | 1 | 1 | 2 | 2 | 3 | 3 | 4 | 4 | 5 | 5 | 6 | 6 | 7 | 7 | 8 | 8 | 9 | 9 | 10 | 10 | 11 | 11 | 12 |
| DETECTOR j | 12 | 13 | 13 | 14 | 14 | 15 | 15 | 16 | 16 | 17 | 17 | 18 | 18 | 19 | 19 | 20 | 20 | 21 | 21 | 22 | 22 | 23 | 23 |
| REBINNED TO BIN GROUP | R22 | L23 | R2 | L2 | R4 | L4 | R6 | L6 | R8 | L8 | R10 | L10 | R12 | L12 | R14 | L14 | R16 | L16 | R18 | L18 | R20 | L20 | R22 |
| RAY NUMBER IN BIN | n/a | 1 | 1 | 2 | 2 | 3 | 3 | 4 | 4 | 5 | 5 | 6 | 6 | 7 | 7 | 8 | 8 | 9 | 9 | 10 | 10 | 11 | 11 |

FIG.15B

| GANTRY POSITION 3 | | | | | | | | | | | | | | | | | | | | | | | | |
|---|---|---|---|---|---|---|---|---|---|---|---|---|---|---|---|---|---|---|---|---|---|---|---|---|
| DETECTOR i | 1 | 1 | 2 | 2 | 3 | 3 | 4 | 4 | 5 | 5 | 6 | 6 | 7 | 7 | 8 | 8 | 9 | 9 | 10 | 10 | 11 | 11 | 12 |
| DETECTOR j | 12 | 13 | 13 | 14 | 14 | 15 | 15 | 16 | 16 | 17 | 17 | 18 | 18 | 19 | 19 | 20 | 20 | 21 | 21 | 22 | 22 | 23 | 23 |
| REBINNED TO BIN GROUP | R21 | R23 | R1 | L1 | R3 | L3 | R5 | L5 | R7 | L7 | R9 | L9 | R11 | L11 | R11 | L11 | R15 | L15 | R17 | L17 | R19 | L19 | R21 |
| RAY NUMBER IN BIN | n/a | 1 | 1 | 2 | 2 | 3 | 3 | 4 | 4 | 5 | 5 | 6 | 6 | 7 | 7 | 8 | 8 | 9 | 9 | 10 | 10 | 11 | 11 |

| GANTRY POSITION 4 | | | | | | | | | | | | | | | | | | | | | | | | |
|---|---|---|---|---|---|---|---|---|---|---|---|---|---|---|---|---|---|---|---|---|---|---|---|---|
| DETECTOR i | 1 | 1 | 2 | 2 | 3 | 3 | 4 | 4 | 5 | 5 | 6 | 6 | 7 | 7 | 8 | 8 | 9 | 9 | 10 | 10 | 11 | 11 | 12 |
| DETECTOR j | 12 | 13 | 13 | 14 | 14 | 15 | 15 | 16 | 16 | 17 | 17 | 18 | 18 | 19 | 19 | 20 | 20 | 21 | 21 | 22 | 22 | 23 | 23 |
| REBINNED TO BIN GROUP | L20 | R22 | L22 | L23 | R2 | L2 | R4 | L4 | R6 | L6 | R8 | L8 | R10 | L10 | R12 | L12 | R14 | L14 | R16 | L16 | R18 | L18 | R20 |
| RAY NUMBER IN BIN | n/a | 1 | 1 | 2 | 2 | 3 | 3 | 4 | 4 | 5 | 5 | 6 | 6 | 7 | 7 | 8 | 8 | 9 | 9 | 10 | 10 | 11 | 11 |

HIGH RESOLUTION PET SCANNER USING ROTATING RING ARRAY OF ENLARGED DETECTORS HAVING SUCCESSIVELY OFFSET COLLIMATION APERTURES

This invention is generally related to computed tomography image systems of the type which acquire image data by detecting photons emitted as a result of decaying radionuclides within an image volume scanned by the image system. Although some aspects of this invention may be useful with single photon emission computed tomography (SPECT) it is more particularly directed to a positron emission tomography (PET) imaging system.

Single photon emission computed tomography (SPECT) and positron emission tomography (PET) are by now well-known in the art. There are extensive literature descriptions of numerous SPECT and PET systems and there are many commercial PET imaging systems now available and in regular use. In typical usage, a quickly decaying radionuclide is created and administered to a patient As the radionuclide is taken into the patient's anatomical system, it becomes distributed in accordance with the patient's unique physiological functions and/or anatomy. For example, the time required for certain radionuclides to distribute (or not to distribute) within certain portions of the brain anatomy has been discovered as a useful diagnostic and/or study tool.

In SPECT imaging systems, a single photon is emitted at an arbitrary orientation from a given anatomical site. Accordingly, to detect the relative direction to a photon source site, one is entirely dependent upon collimation and/or Anger-type cameras capable of deducing the location of a detector scintillation by analyzing the outputs of a spatial array of photo-multiplier tubes (PMTs) optically coupled to one or more scintillation detector crystals.

However, in PET imaging, a positron from a decaying radionuclide quickly encounters and annihilates with an electron resulting in a pair of 511 KeV annihilation photons which are always emitted in exactly opposite (180°) directions from the annihilation site. Accordingly, by arranging banks of scintillation crystals (optically coupled to PMTs) all around an image volume, substantially simultaneous detections of photons in opposingly situated detectors inherently define the site of the positron/electron annihilation as lying somewhere along a line directly between the opposing detectors associated with the substantially simultaneous events (e.g., events occurring within an about one nanosecond time window).

In general, any imaging system can be improved by improving its ability to provide higher resolution images. With more resolution and therefore more detailed images, utility is enhanced.

As is well understood in the art, the Nyquist sampling theorem generally requires a spatial sampling frequency at least twice the highest spatial frequency in the reconstructed image (with some possible relaxation if iterative successive approximation reconstruction techniques are utilized). This means that the interval between projection image data samples must be about half the expected image resolution. That is, to achieve image resolution on the order of 2 millimeters, one must acquire projection image data with sample intervals on the order of 1 millimeter spacing.

In general, past attempts to increase the resolution capability of SPECT systems have involved ever more sophisticated and complex rotating Anger type camera and collimators (with cone and/or complex multi-axis foci) in combination with arrays of N scintillator crystals optically coupled to M PMTs.

To take advantage of the inherent directionality included in PET image data, traditional attempts to obtain higher resolution have involved increasing numbers of smaller individual scintillator crystals. By making the crystals ever smaller and by coupling them with PMTs so as to determine exactly which individual crystal has produced a scintillation photon (as a result of an incident gamma ray photon) at any given precise time it is possible to more accurately locate the line along which the annihilation photons have traveled. In this way, when substantially simultaneous scintillations are detected in opposing small discrete crystals, the locus of a rayline along which the positron/electron annihilation must have occurred can be more accurately recorded.

A sample of published literature generally describing such past attempts is set forth below:

Cho et al—"High-Resolution Circular Ring Positron Tomograph With Dichotomic Sampling: Dichotom-I," Phys. Med. Biol.

1983, Vol. 28, No. 11, pp 1219–1234.

Tanaka—"Recent Progress on Single Photon and Positron Emission Tomography - From Detectors to Algorithms—," IEEE Transactions on Nuclear Science, Vol. NS-34, No. 1, Feb. 1987, pp 313–320.

Genna et al—"The Development of Aspect, An Annular Single Crystal Brain Camera For High Efficiency Spect," IEEE Transactions on Nuclear Science, Vol. 35, No. 1, Feb. 1988, pp 654–658.

Rogers et al—"Conceptual Design of a Whole Body PET Machine," IEEE Transactions of Nuclear Science, Vol. 35 m, No. 1, Feb. 1988, pp 680–684.

Muehllehner et al—"Design and Performance of a New Positron Tomograph," IEEE Transactions on Nuclear Science, Vol. 35, No. 1, Feb. 1988, pp 670–674.

Derenzo et al—"A Positron Tomograph with 600 BGO Crystals and 2.6MM Resolution," IEEE Transactions on Nuclear Science, Vol. 35, No. 1, Feb. 1988, pp 659–664.

Derenzo et al—"Initial Results From the Donner 600 Crystal Positron Tomograph," IEEE Transactions on Nuclear Science, Vol. NS-34, No. 1, Feb. 1987, pp 321–325.

Muehllehner et al—"Advances In SPECT and PET," IEEE Transactions on Nuclear Science, Vol. 35, No. 1, Feb. 1988, pp 639–643.

Lewellen et al—"Performance Measurements Of The SP3000/UW Time-Of-Flight Positron Emission Tomograph," IEEE Transactions on Nuclear Science, Vol. 35, No. 1, Feb. 1988, pp 665–667.

Burnham et al—"Cylindrical PET Detector Design," IEEE Transactions on Nuclear Science, Vol. 35, No. 1, Feb. 1988, pp 675–679.

Carrier et al—"Design of a High Resolution Positron Emission Tomograph Using Solid State Scintillation Detectors," IEEE Transactions on Nuclear Science, Vol. 35, No. 1, Feb. 1988, pp 685–690.

Cho et al teach a PET system having a ring array of scintillator crystal/PMT gamma ray detectors arranged in a plurality of separately rotatable sub-arrays. By incrementally rotating the subarrays with respect to one another, a larger number of sampling points is created Each scintillation crystal is also collimated with a centrally located aperture (see FIG. 5 of Cho et al) so as to further enhance the resolution capability of this system.

Genna et al teach a SPECT camera system having but a single continuous ring scintillator crystal optically coupled to 3 ring arrays of 21 photo-multiplier tubes each. A rotating multi-field Anger-type collimator is employed so as to introduce image resolution into the system. Although a relatively small number of only 21 PMTs per ring is required, the resulting resolution at the center of rotation is only expected to be about 6 millimeters. Both continuous as well as incremental motion of the multi-field collimator is described.

Rogers et al teaches a PET system which is designed to use smaller numbers of larger scintillation crystals in conjunction with uniform rotational motion. An imaging PMT is optically coupled to a relatively large area NaI scintillation crystal so as to permit the location of a given scintillation event within the larger crystal. It does not appear that any collimation is contemplated for sample resolution purposes.

Muehllehner et al teach yet another PET system design utilizing a relatively small number of large scintillation crystals. Here, 6 large scintillation crystals are arranged in a hexagonal ring array. Each crystal is coupled to a 3×10 array of PMTs which apparently utilize Anger-type logic to locate the situs of individual scintillation events within the large crystal. There does not appear to be any collimation involved.

There have also been a number of issued patents relevant to this technology. Some examples are listed below:

U.S. Pat. No. 3,585,387—Bramlet (1971)
U.S. Pat. No. 4,295,047—Koga et al (1981)
U.S. Pat. No. 4,309,611—Tanaka et al (1982)
U.S. Pat. No. 4,389,569—Hattori et al (1983)
U.S. Pat. No. 4,352,018—Tanaka et al (1982)
U.S. Pat. No. 4,473,749—Derenzo et al (1984)
U.S. Pat. No. 4,514,632—Barrett (1985)
U.S. Pat. No. 4,531,058—Burnham et al (1985)
U.S. Pat. No. 4,584,478—Genna et al (1986)
U.S. Pat. No. 4,733,083—Wong (1988)
U.S. Pat. No. 4,743,764—Casey et al (1988)
U.S. Pat. No. 4,748,328—Chang et al (1988)
U.S. Pat. No. 4,749,863—Casey et al (1988)
U.S. Pat. No. 4,774,410—Hsieh (1988)
U.S. Pat. No. 4,782,233—Genna et al (1988)

Hattori et-al, Tanaka et al, Chang et al, Hsieh and Genna et al appear to teach ring array detector structures having some asymmetries and thus are presently believed to perhaps be more pertinent than others to this invention.

In spite of such attempts to achieve lower cost and higher resolution imaging systems, typical presently available systems actually have resolution of only 2 to 3 millimeters (and more typically 5 to 6 millimeters for commercially available systems) with costs in the range of one to six million dollars per imaging system. Typically, this degree of resolution is achieved only by having a very large number of very small crystals (e.g., 500 or 600 hundred) in each of plural ring arrays axially distributed about an image volume. With such a large number of crystal/PMT signal channels to process, the complexity and cost of the required electronics is extremely high even if only the simplest type of processing is utilized in each channel to produce image data (which is thereafter utilized in any desired conventional image reconstruction algorithm such as filtered back projection or the like). Furthermore, as crystal size is made smaller, its photon-stopping ability is reduced thus decreasing detection efficiency and also making it more difficult to reject detection of scattered photons.

Frustrated by the relatively high cost of systems capable of achieving only relatively rough resolution, some investigators have recently turned to non-imaging systems using but a pair of relatively larger crystals in conjunction with collimation and greatly simplified electronics. See, for example:

Bice et al, "Simplified Detection System for Neuroreceptor Studies in the Human Brain," The Journal of Nuclear Medicine, Vol. 27, No. 2, Feb. 1986, pp 184–191.

Bice et al use a pair of large (3" × 3") NaI scintillator crystals oppositely positioned with respect to a patient's head. Each of these large scintillator crystals is optically coupled to its own PMT thus providing only two channels of electrical signals for coincidence processing, counting, etc. Although, this simple system is not capable of imaging, it can nevertheless provide useful diagnostic information if its field of view is properly located and focussed upon a proper portion of a patient's anatomy (e.g., in the brain). Extremely simple electronics can be utilized for this application such that the entire non-imaging system can be made very cheaply (e.g., $25,000) compared with typically available PET imaging systems (e.g., 1 to 6 million dollars). It appears that Bice et al relied upon collimators and coincidence detection to limit the effective field of view of the crystal pair to the desired patient anatomy. A larger detection sensitivity permitted by the larger crystals also permits lower radionuclide doses to the patient.

In considering the economies and advantages associated with the non-imaging Bice et al type of system, we have come to appreciate the possibility of achieving similar operating and functional advantages as well as cost economies in a PET imaging system. Indeed, we have discovered that it is not only possible to achieve imaging capability while yet retaining functional and cost advantages, it is possible to do so even while greatly enhancing the resolution capability of the resulting PET imager beyond that typically available with even the most complex and costly PET imagers of the prior art.

In brief summary, we have discovered an improved PET imaging system which utilizes a ring array of collimated gamma ray detectors mounted for rotation about an image volume and having respective collimation apertures located at different relative inter-aperture spacings as a function of detector location within the ring array so as to result in rebinned sets of substantially parallel projection image data by mere linear rotation of the array through successive view angles.

A ring array of relatively large and fast scintillation crystals (each coupled to its own PMT) may be incrementally rotated between predetermined view angle positions or continuously rotated with appropriate sampling time windows determined as a function of angular position. Because the inter-aperture spacings are sequentially offset around the array, similarly offset projection image data is obtained as the array is rotated. By "re-binning" (i.e., regrouping or resorting individual members of data sets taken at one sample time into other sets or groups representing a desired sampling of the image volume at a given view angle), virtually any suitable conventional image reconstruction algorithm can be utilized to reconstruct an image representing a distribution of decaying radionuclides within a cross-section of the image volume.

For example, the originally acquired data sets may be re-binned so as to provide projection image data for a plurality of equally spaced-apart substantially parallel ray lines at each of a succession of view angles through an image volume. As is well-known in the art, there are many filtered back projection or other image reconstruction algorithms which may be utilized in conjunction with such data to produce a reconstructed image for conventional display or recordation (e.g., on a CRT screen, in film, in digital memory media, etc).

Furthermore, since only a relatively small number of electrical signal processing channels are involved, one can more economically include evermore sophisticated processing circuits. For example, time of flight (TOF) filters may be employed in each channel so as to discriminate against positron emission data emanating from outside a desired portion of a image volume being viewed by the detector array.

In the exemplary embodiment, a first sequentially located approximately half of the ring array detectors have respective collimator aperture offsets which progressively change in one sense with respect to the detector centers. The remaining sequentially located ring array detectors have respective collimator aperture offsets which progressively change in a second sense, opposite to the first sense, with respect to their detector centers. Because of the differential inter-aperture spacing around the ring array, the image volume is spatially sampled at successively offset positions at any given view angle. Thus, by recording and rebinning sequentially acquired data as the ring array is successively rotated through the range of view angles, a properly distributed spatial sampling of the image volume can be obtained for input to conventional computed tomography reconstruction algorithms.

Although the preferred and exemplary embodiments utilize collimators permanently affixed to scintillator crystal detectors (each of which is also permanently affixed to its respective PMT), it may be possible to achieve similar results with a ring array of collimator elements rotated with respect to a fixed ring array of scintillator crystal/PMT's (with some possible further complexity in the electronic processing channels).

The exemplary embodiment of our invention provides a low-cost but high-resolution mini-brain PET imaging system. It uses relatively large and relatively fast scintillation crystal detectors (each with its own PMT) in conjunction with sequentially arranged shadow collimator rotating ring detector (SASCRRD) geometry to nevertheless achieve high-resolution sampling. For example, although the exemplary embodiment uses only twenty-three 5-centimeter diameter BaF$_2$ detectors in conjunction with a simple mechanical gantry capable of only linear rotational motion (all of which reduces major system costs significantly), it is nevertheless capable of approximately 1 millimeter sampling (i.e., image resolution on the order of 2 millimeters FWHM).

Each detector in the mini-brain PET imager can achieve almost 100% detection efficiency because of the large scintillation crystal volume (i.e., very high probability of stopping any incident 511 KeV photon). It also achieves virtually 100% scatter rejection because the high detector efficiency permits excellent energy discrimination (by selection of photo-peak components only) without significant loss of detection efficiency.

The exemplary embodiment also permits virtually 100% random coincident event rejection because it is capable of much improved time resolution (e.g., BaF$_2$ has a 200 pico-second FWHM time resolution which is a factor of 10 better than that of NaI(Tl) crystals.)

Furthermore, full advantage can be taken of this faster detector timing by providing the most sophisticated time of flight processing circuits to each of the relatively small number of processing channels. In this fashion, scatter backgrounds can be substantially eliminated and imaging capability can be substantially enhanced by filtering out coincidences emanating from outside a portion of the image volume actually of interest (e.g., outside the central 5 centimeter diameter portion of the image volume).

The exemplary embodiment can also be converted to a medium or low resolution mode by simply changing the collimator openings. Such lower resolution modes might be desired, for example, so as to obtain correspondingly higher sensitivity (i.e., instead of the highest possible resolution). A multiple aperture (per detector) embodiment is also proposed to help improve sensitivity.

The exemplary embodiment, although capable of imaging to the highest possible resolution, is also sufficiently economical as to be useful for fast, dynamic, regional, brain activity monitoring of the type contemplated by Bice et al (albeit with an order of magnitude improvement in overall detection efficiency or speed due to the large number of detectors contemplated for the exemplary embodiment —and with the optional ability to image as well, if desired).

In the exemplary embodiment, approximately 1 millimeter sample intervals are obtained substantially uniformly at numerous view angles through a central 5 centimeter diameter image volume which, it will be noted, is approximately the same diameter as the array-dimension of the enlarged scintillator crystal!. This fine sampling interval is nevertheless achieved by a sequentially shifted arrangement of collimator openings as a function of position around the ring array combined with simple linear rotational scan motion of the ring array. Although, only the central portion of the image volume (e.g., the central 5 centimeter diameter portion), is sufficiently sampled to provide the highest resolution image, data is nevertheless simultaneously provided for medium resolution imaging outside the central region, if desired.

In our exemplary embodiment, we have discovered that the optimum number of detectors for an inside array diameter of about 35 centimeters (or for even as small as 22 centimeters diameter), a high resolution image volume of about 5 centimeters and a resolution on the order of about 2.5 millimeters is 23 detectors, each detector being of about 5 centimeters in the array-dimension As will be appreciated after understanding this invention, the optimum number of detectors is, to a large extent, a function of the desired inside diameter of the array, the desired maximum size of the high resolution central image volume and desired resolution within that portion of the image volume.

These as well as other objects and advantages of this invention will be more completely understood and appreciated by careful study of the following detailed description of a presently preferred exemplary embodiment, taken in the accompanying drawings, of which:

FIG. 15A and 15B depict a look-up table useful for rebinning the coincident lines of projection data in the exemplary embodiment;

FIGS. 16A, 16B and 17 depict a rebinning flow diagram for the exemplary embodiment;

Figure 1:
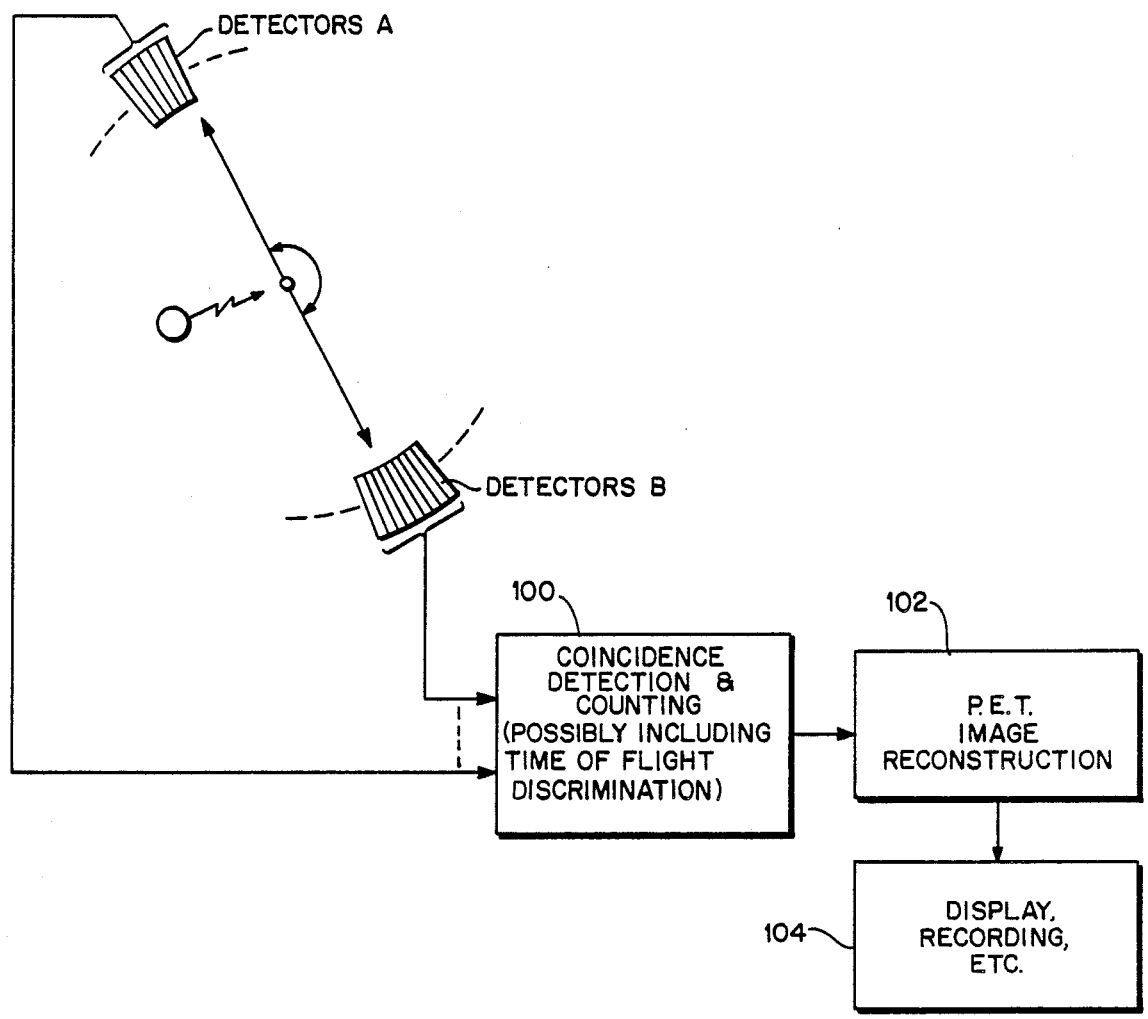
FIG. 1 is a schematic depiction of a typical prior art PET imaging system.

A typical prior art PET imaging system is schematically depicted at FIG. 1. Here, a decaying radionuclide in the image volume emits a positron which soon encounters an electron with the usual annihilation producing a pair of exactly oppositely directed 511 KeV gamma ray photons. Typically, the image volume is surrounded by a ring array of many (e.g, 500 or 600) scintillation detector crystals (either individually associated with PMTs or collectively via Anger-type logic associated with a smaller array of PMTs in an outer ring PMT array).

Thus, the pair of 511 KeV annihilation photons from a given annihilation event will reach oppositely disposed detectors A, B at approximately the same time. The only time difference is due to the different travel times or "time of flight" at the speed of light from the actual annihilation location if located off-center. The outputs of these detector arrays are conventionally processed by coincidence detection and counting circuits 100 which in this case include time-to-amplitude converters (possibly also including time-of-flight filtering by time discrimination).

The resulting image data (typically projection data from substanitally uniformly dispersed ray lines through the image volume) is utilized by conventional image reconstruction algorithms at 102 (e.g., filtered back projection) to produce the usual display or recorded image, etc., at 104. As previously explained, the use of increasingly numerous detectors so as to enhance image resolution inherently greatly increases the complexity and cost of the necessary signal processing circuits 100 (thus possibly making it economically impossible to use sophisticated time of flight filtering or imaging)—while at the same time also degrading individual detector efficiency, and reducing the ability to reject scattered photons or random coincidence detections.

Figure 2:
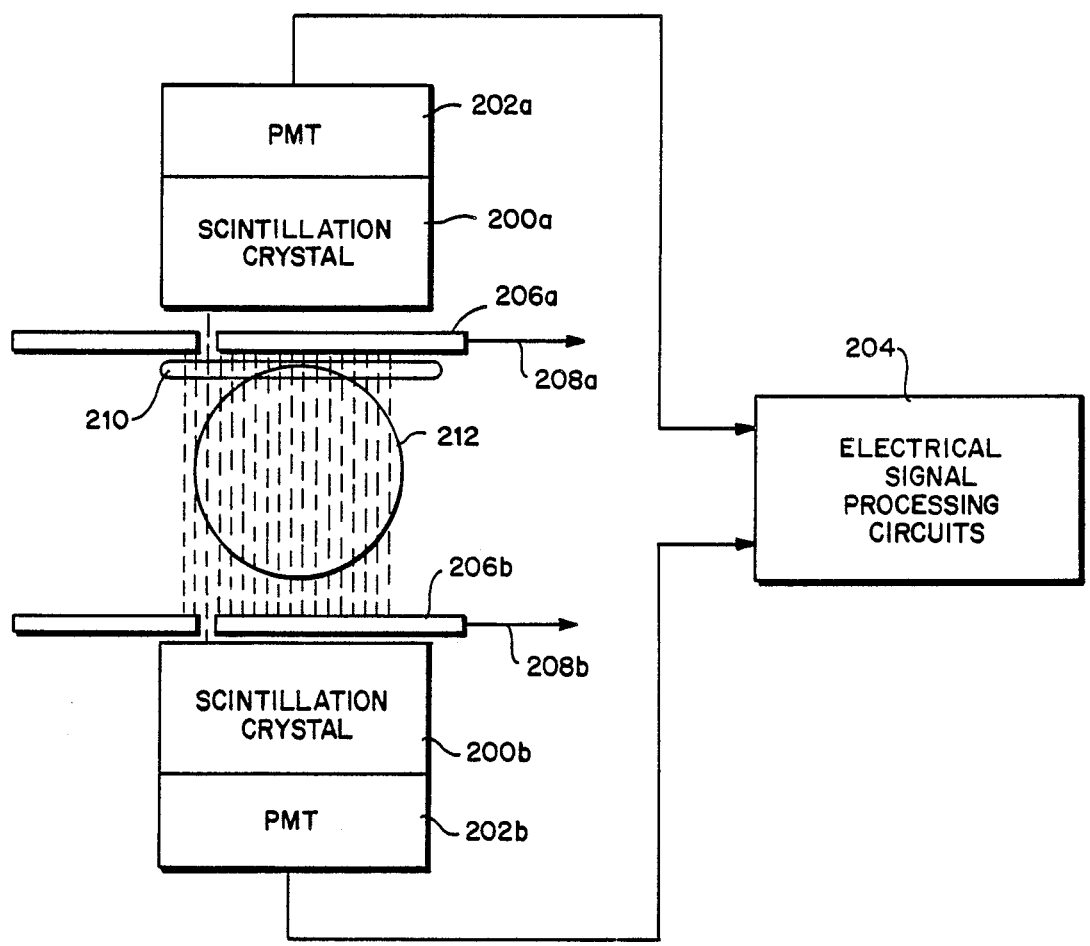
FIG. 2 is a schematic illustration of a pair of larger opposingly situated detector crystals in conjunction with means for achieving successively offset collimation which, at any given sample time, substantially occludes most of the larger detector surface in an explanatory/simplified version of our invention.

On the other hand, if relatively larger and fast scintillation crystals 200A, 200B are utilized as in FIG. 2, then detector efficiency and the ability to discriminate against scattered photons and random coincidence detections is greatly enhanced (assuming faster scintillation crystals such as $BaF_2$ and PMTs 202A, 202B are utilized in conjunction with sufficiently sophisticated electrical signal processing circuits 204).

Of course, with fixed collimation, this would be the non-imaging Bice et al system previously discussed with respect to the prior art.

However, by moving collimators 206A, 206B to successive sample points as indicated by arrows 208A, 208B, one can acquire a set of equally spaced projection image data along ray lines 210 through image volume 212. By incrementally rotating the pair of detectors/translatable collimators and repeating the collimator translation, similar sets of projection image data along a succession of view-angles could be obtained for conventional image reconstruction (e.g., using filtered back projection).

However, we have discovered that a substantially equivalent result can be achieved using only simple linear rotational motion by using a ring array of scintillation crystal/PMTs with respectively affixed collimators having successively offset collimator apertures. In this manner, at any given sampling instant, one ray-member of the projection image data set 210 (or a close approximation thereof) can be acquired for any given view angle. Another ray-member of the set (or a close approximation thereof) will be acquired with a different combination of opposing collimated detectors at each successive view angle sampling point during simple linear rotation of the ring array. By "rebinning" these successively acquired ray-members of a given set after a complete rotation, all of the ray-members of the set 210 (or their near approximations can) be acquired and made available for conventional image reconstruction algorithms.

Figure 3:
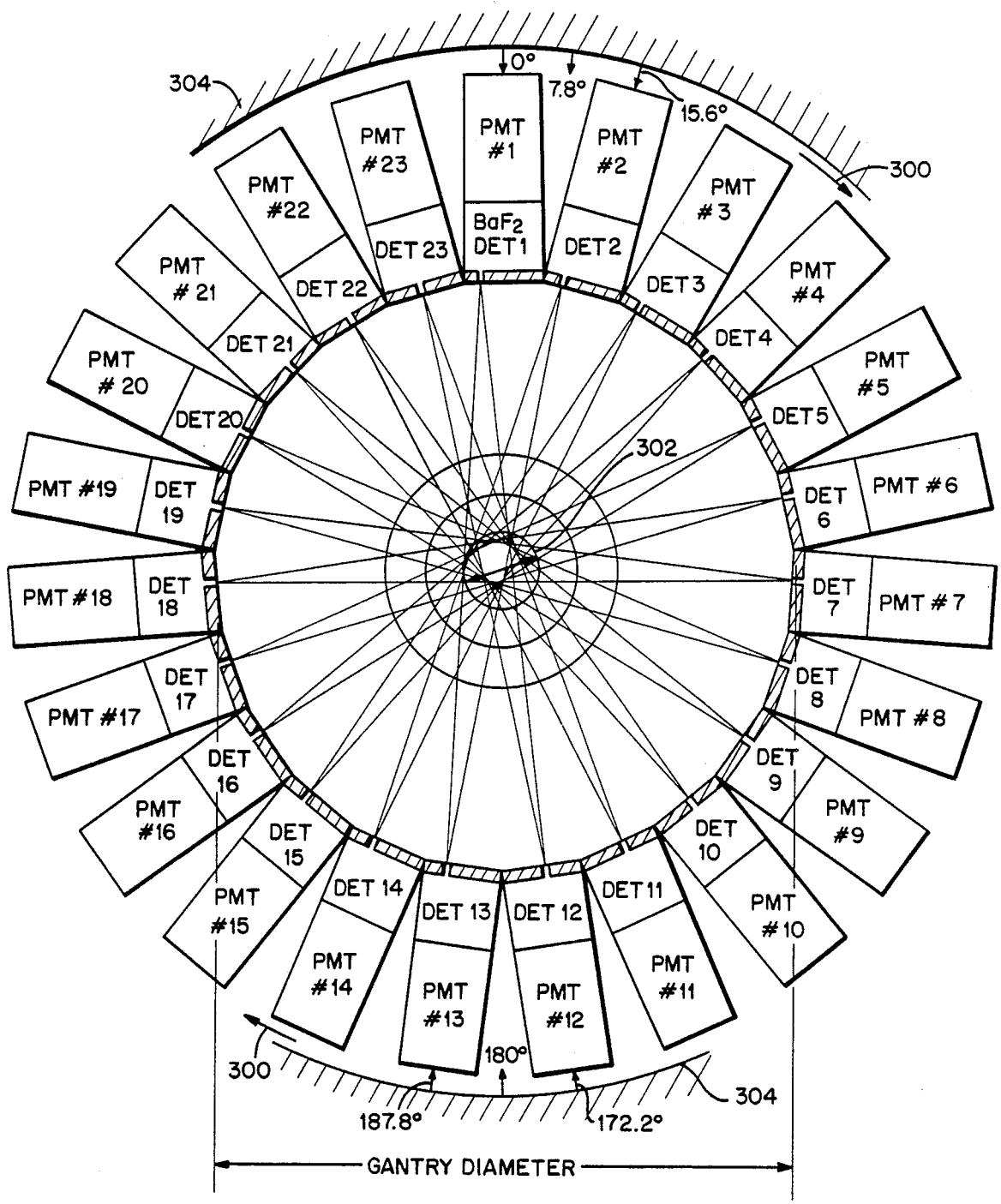
FIG. 3 is a schematic depiction of a 23 detector ring array proposed for a presently preferred exemplary embodiment of this invention.

One exemplary embodiment of such a system is depicted at FIG. 3. Here, there are twenty-three (23)

barium floride (BaF$_2$) scintillation crystal detectors (sequentially numbered for reference purposes as depicted in FIG. 3). Each scintillation crystal is approximately 5 centimeters in diameter and is coupled to its own photo-multiplier tube (the PMTs also are sequentially numbered for reference purposes as depicted in FIG. 3).

As depicted by arrows 300, this entire ring array of detectors/PMTs is mounted for simple linear rotational motion with respect to a central image volume 302 and with respect to a fixed PET system gantry frame 304. For reference purposes, certain fixed angular view angle locations are depicted on the fixed portion of gantry frame 304 at intervals of 7.826° (e.g., at intervals equal to half the angular spacing between elements of the detector/PMT ring array).

Figure 4A:
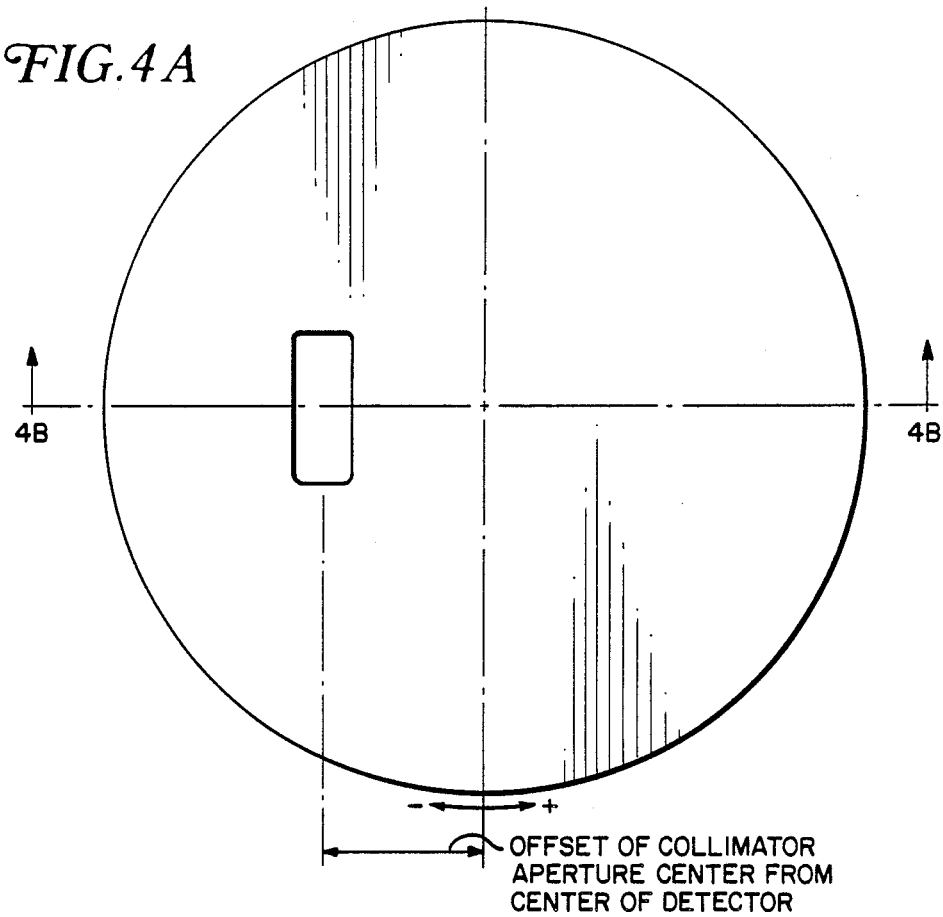
FIGS. 4A and 4B are plan and cross-sectional views respectively of an exemplary collimator with offset aperture as used in the exemplary embodiment of FIG. 3.
Figure 4B:
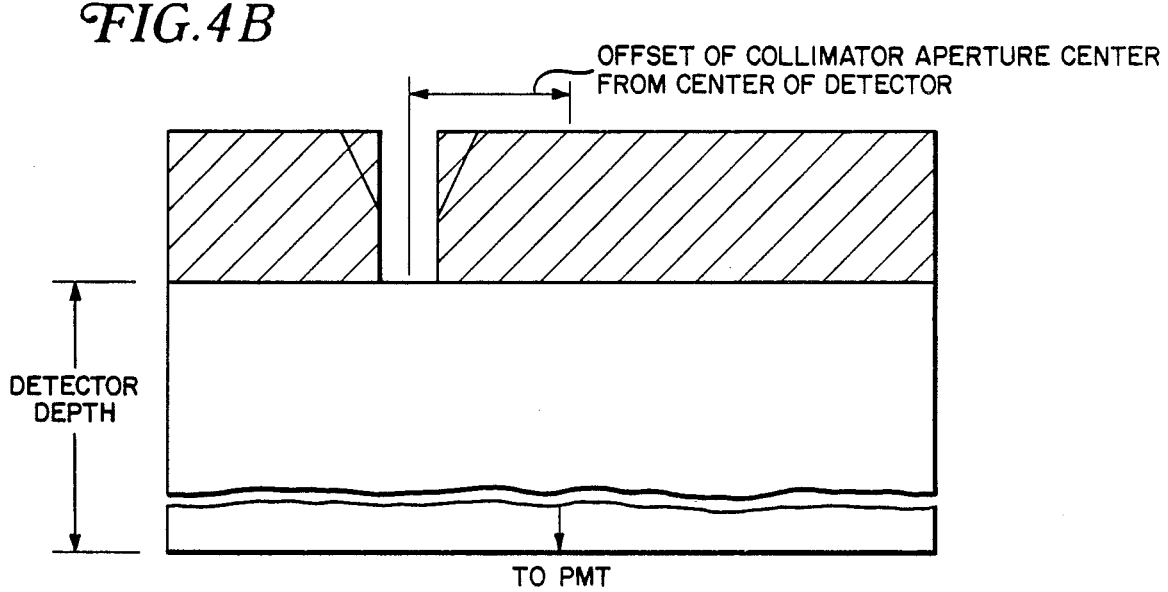
Figure 5:
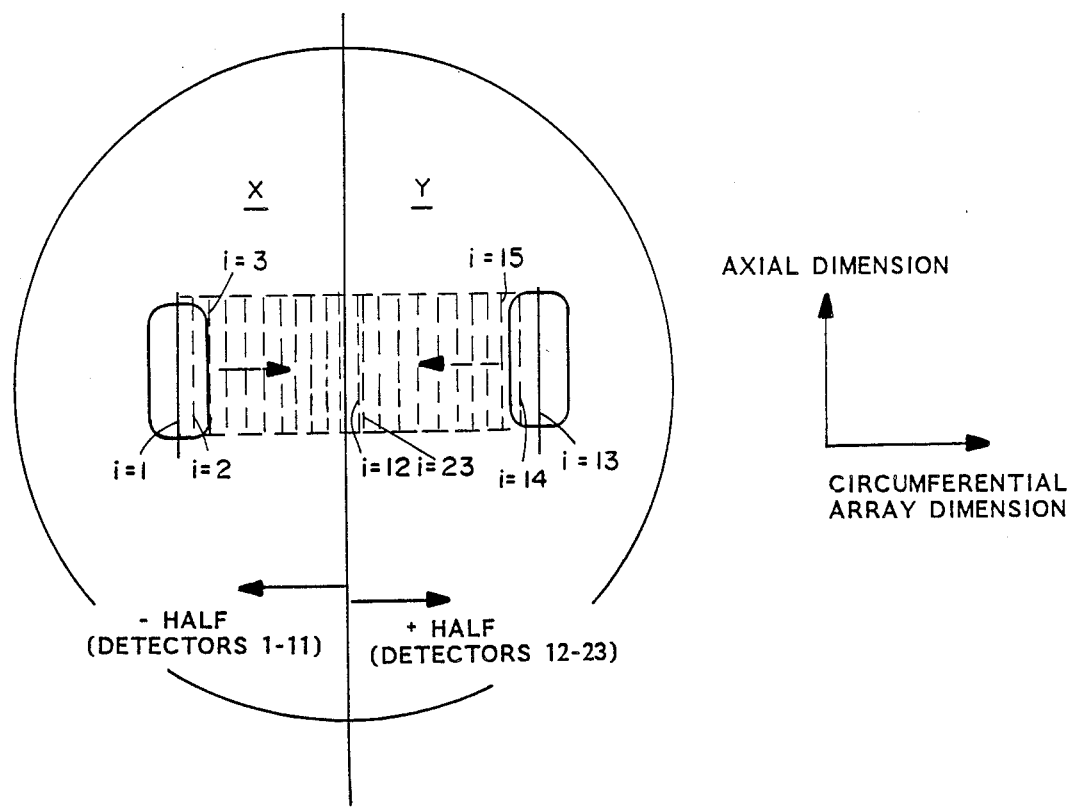
FIG. 5 is a schematic diagram of a collimator similar to the plan view of FIG. 4A but depicting the manner in which the aperture offsets progress for different ones of the 23 detectors in the exemplary embodiment of FIG. 3.

As depicted in FIG. 3, each scintillation detector crystal has affixed to it a collimator. In fact, the collimator occludes all of the scintillator crystal except for a small aperture which is located at different relative inter-aperture spacings as a function of detector location within the ring array. For example, it will be noted that the aperture for detector 1 is offset a certain maximum distance from the detector center line and that this offset distance progressively decreases for detectors 2, 3, 4, 5, 6, 7, 8, 9, 10, 11 and 12. Similarly, the aperture for detector 13 is offset to a maximum dimension in an opposite sense from the detector center which offsets successively decrease for detectors 14, 15, 16, 17, 18, 19, 20, 21, 22 and 23. Exemplary collimator and detector dimensions and suitable formulae for determining the successive offset dimensions in this exemplary embodiment are depicted at FIGS. 4A, 4B and 5. It should be noted that the interval between collimator centers for detectors 12 and 23 is less than other intervals so as to obtain more substantially equally spaced sampling intervals in the rebinned projection image data.

Figure 6A:
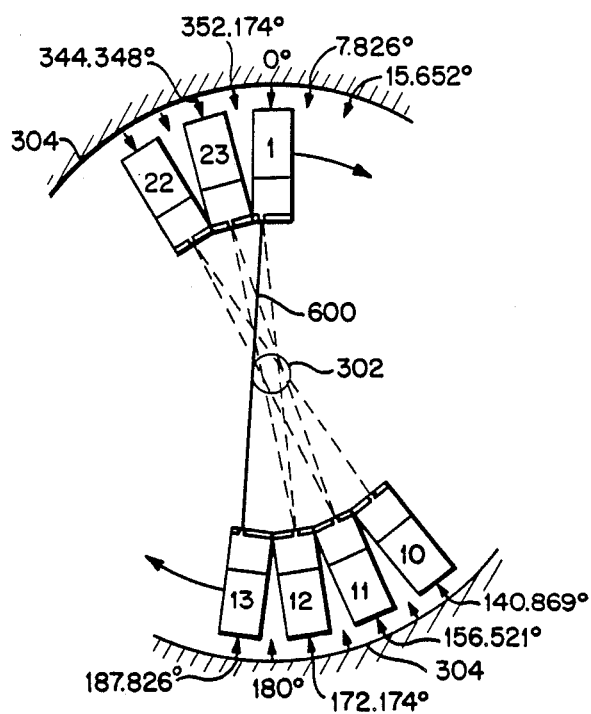
FIGS. 6A, 6B, 6C and 6D illustrate six successive view angle positions of the FIG. 3 detector ring array with successively acquired projection data for one particular view angle being depicted in solid line between respective detector collimator apertures.
Figure 6B:
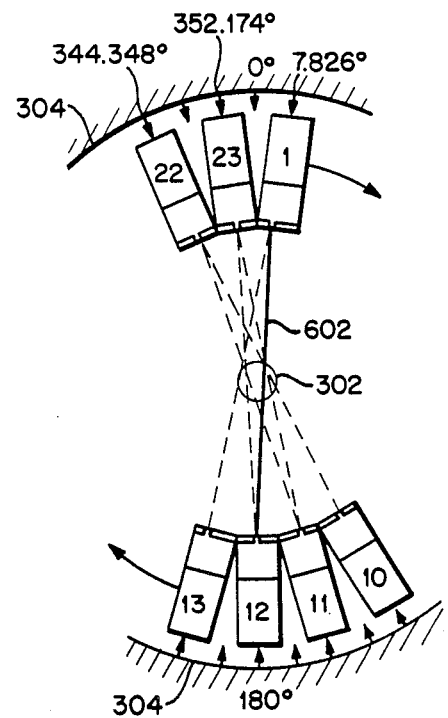

To help illustrate the manner in which a set of substantially parallel (e.g., to within an angular error of ±0.1° or less) projection ray image data can be obtained, a succession of FIGS. 6A, 6B, 6C and 6D show four successive view angle positions of the ring array with respect to image volume 302. Thus, in a position shown at FIG. 6A, coincident detected scintillations between detectors 1,13 define a ray member 600 passing at a particular angle through the image volume. After sufficient data is accumulated at this position, the ring array is further rotated (either continuously or incrementally) to a subsequent view angle position as shown in FIG. 6B. Here, ray member 602 is defined by coincident events from detectors 1,12 passing at substantially the same angle as ray member 600 through image volume 302 (but now slightly offset to the right of its center).

Figure 6C:
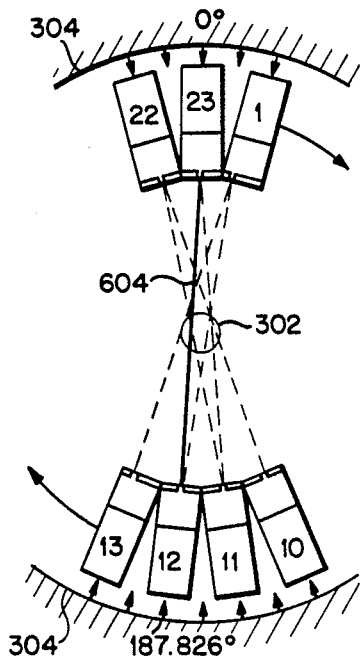
Figure 6D:
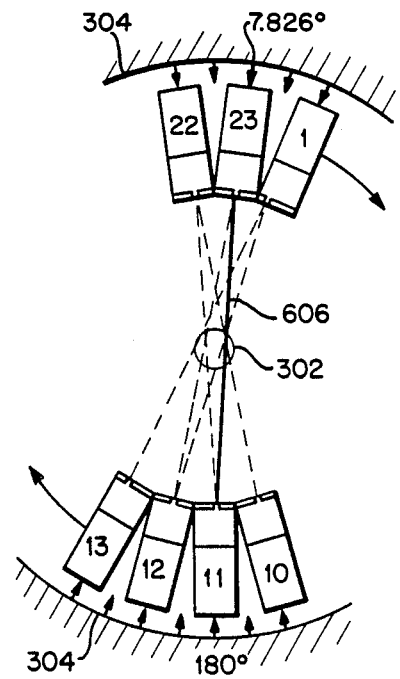
Figure 7:
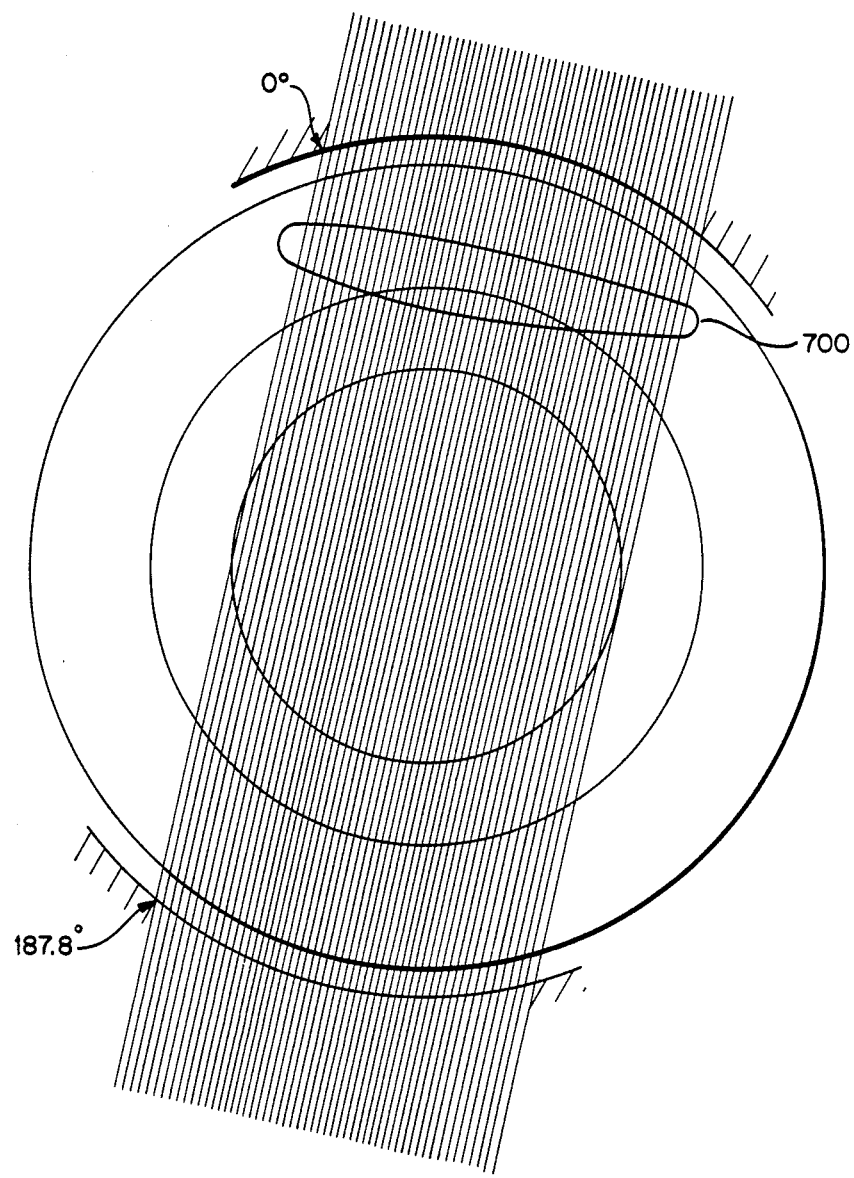
FIG. 7 is a schematic depiction of the resulting read end set of equally spaced-apart parallel ray lines along which the 5 centimeter central image volume is sampled as a result of a continued succession of rotation and sampling as depicted in FIGS. 6A-6D in the exemplary embodiment.

After sufficient coincidence data is detected in the position of FIG. 6B, the ring array is further rotated to the position detected at FIG. 6C where coincident events between detectors 23,12 define ray members 604 also passing at substantially the same angle as ray member 600 and 602 through image volume 302 (albeit now to the left of its center and to the right of ray member 600). Further rotation to the position shown at FIG. 6D defines ray member 606 (also at the same angle as ray members 600, 602, and 604) through image volume 302 (also on the right of center and to the right of ray member 602).

As should now be apparent, by continuing the process depicted in FIGS. 6A-6D, a complete set of equally spaced-apart substantially parallel ray members 700 can be acquired (e.g., over substantially 360° revolution of the ring detector array). As should also be appreciated, similar sets of substantially parallel projection data can simultaneously be acquired for each of the other initial angular ray members depicted in FIG. 3 thus representing a succession of sets of projection image data from a succession of different view angles. This is, of course, exactly the sort of data that is required for conventional image reconstruction algorithms (e.g., filtered back projection, iterative successive approximation, etc). It should also be apparent that by increasing the number of view angle sample points (or decreasing the sample times or rotary speed in the case of continuous rotary motion), increased numbers of view angles may also be defined.

Figure 8:
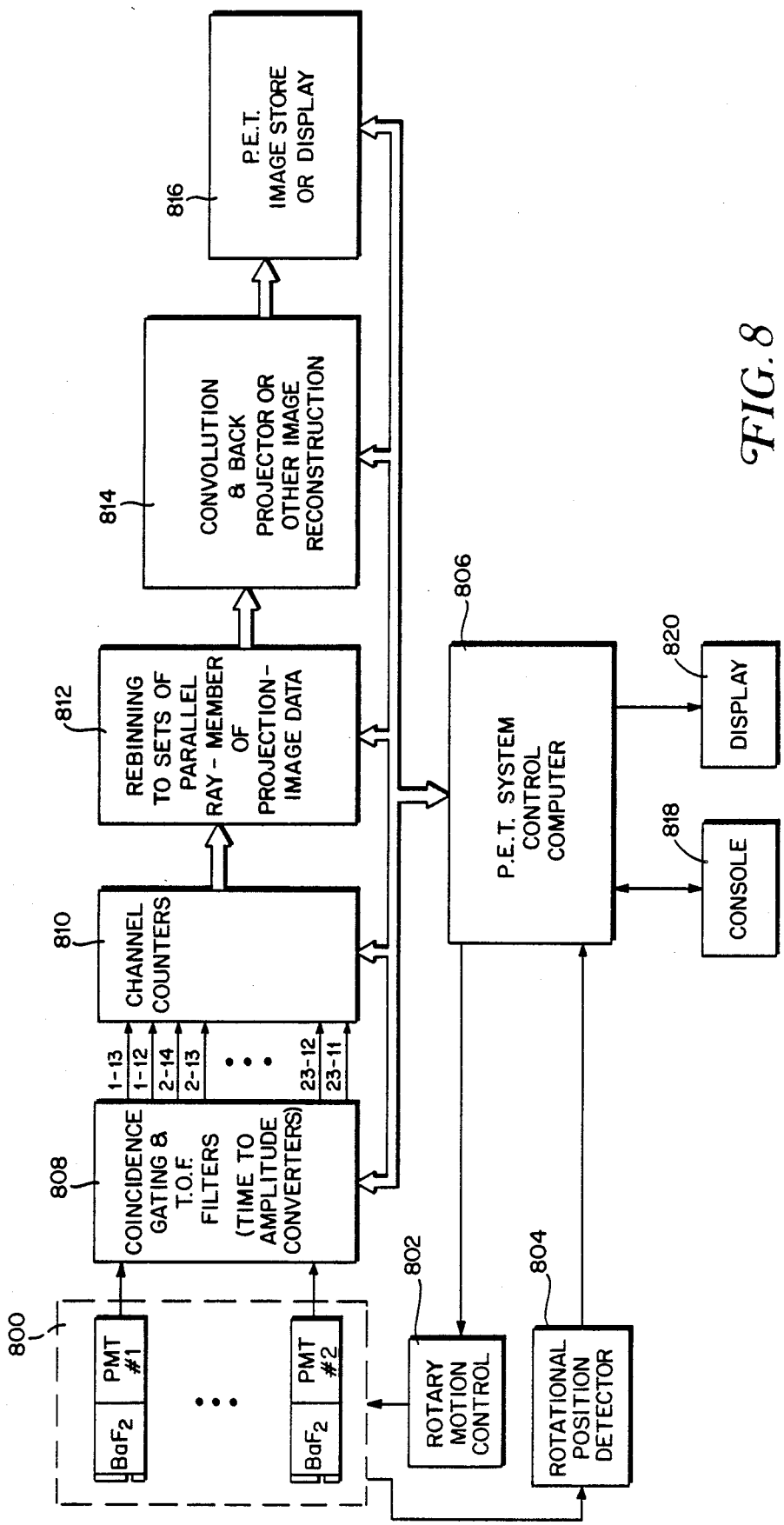
FIG. 8 is a block diagram of a complete PET imaging system in accordance with the exemplary FIG. 3 embodiment.

The ring array of collimated scintillation detector/PMT detectors is schematically depicted at reference numeral 800 in FIG. 8. Since only simple linear rotary motion is required, these elements may be mounted on a simple rotary motion gantry of conventional design driven by conventional rotary motion control devices 802 (e.g., suitable motors, cogged belts, gears, bearings, etc). One or more conventional rotary position detector 804 may also be utilized in conjunction with the rotary gantry so as to provide feedback to a PET system control computer 806 (useful in generating motion control drive for devices 802 as should be appreciated).

The gantry 800 would typically be suited for slightly more than 360° of rotation and then arranged to be "reset" to its initial position for another scanning cycle (thus avoiding the need for brushes, ring contacts and the like to effect electrical connection to the electrical signal processing circuits).

The 23 detector channels may be processed by conventional coincidence gating and time of flight filters 808. In this regard, it is noted that although time of flight filters are well-known and conventional (e.g., they may be obtained from Ortec, Inc. of Oakridge, Tenn. or Canvra, Inc. of Newhaven, Conn.), they are relatively expensive (e.g., $1,000 per channel) so as to become exorbitantly expensive if great numbers of processing channels are involved (e.g., as is typical in prior art higher resolution PET imaging systems). However, because only a relatively small number of channels is required for each ring of our novel system, sophisticated time of flight filters and/or other more sophisticated signal processing circuits can be economically employed.

Coincident events occurring along the ray lines depicted in FIG. 3 between pairs of oppositely situated detectors are then counted (as is conventional) at 810 for a statistically sufficient time interval so as to acquire projection data from along the associated ray lines.

Either concurrently or subsequently, the resulting projection image data is "rebinned" at 810 so as to produce a set of parallel ray-member projection image data at 812 suitable for conventional image reconstruction at 814 (e.g., convolution and back projection) followed by conventional image storage or display at 816.

As will be appreciated by those in the art, all of the processes just discussed are under suitable control of the PET system control computer 806 via conventional console 818 and display 820. Indeed, the rebinning, filter back projection and image store and display may actually occur internally as a part of the PET system control computer 806 (or one of its sub-processors) as should be appreciated by those in the art.

Figure 9:
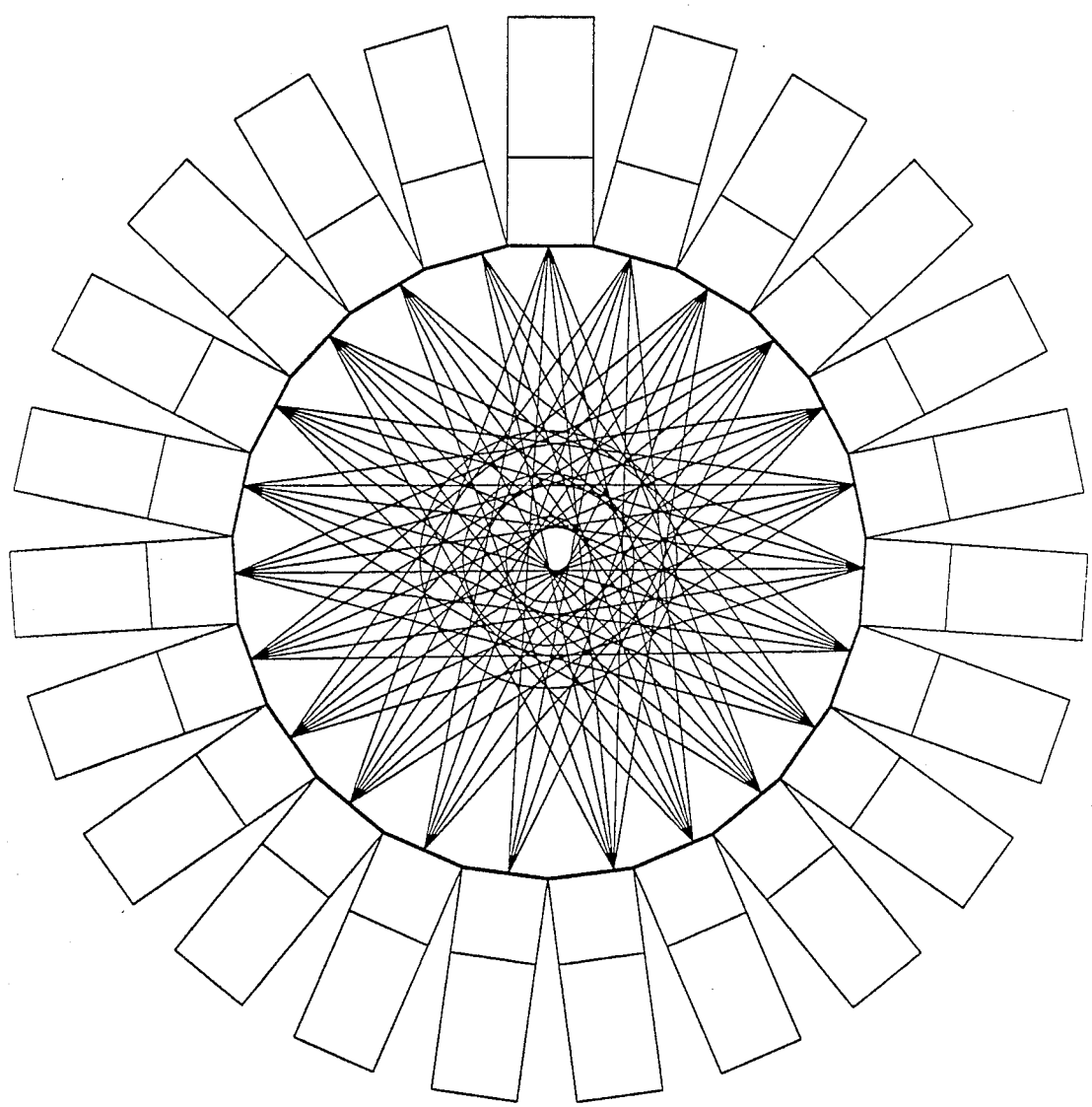
FIG. 9 is a schematic drawing similar to FIG. 3 but now depicting the coincidence lines which may be used simultaneously to obtain a wider (e.g., 15 centimeter diameter) image volume (e.g., such as might be utilized to obtain a rough resolution whole head image useful in positioning the patient for later high resolution imaging within the central smaller (e.g., 5 centimeter diameter) image volume.

As has already been explained, the exemplary system of FIG. 3 may be used to obtain the highest resolution image from the central 5 centimeter image volume. However, as depicted in FIG. 9, coincidence lines can also be defined over a wider image volume (e.g., 15 centimeters). Accordingly, with suitable processing adjustments, a larger image of less resolution can simultaneously be obtained so as to guide positioning of the proper patient anatomy within the higher resolution image volume.

Figure 10:
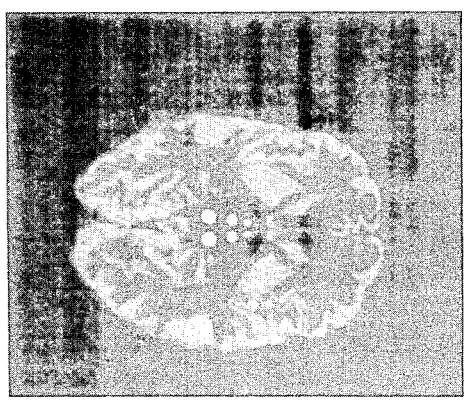
FIG. 10 is a photograph of a simulated image (reconstructed using conventional filtered back projection) from a 92 view (128 rays per view) simulation (the Hoffman phantom here simulated includes resolution indicators having diameters of 2, 4, 6 and 8 millimeters at separations of 2, 4, 6 and 8 millimeters, respectively)
Figure 11:
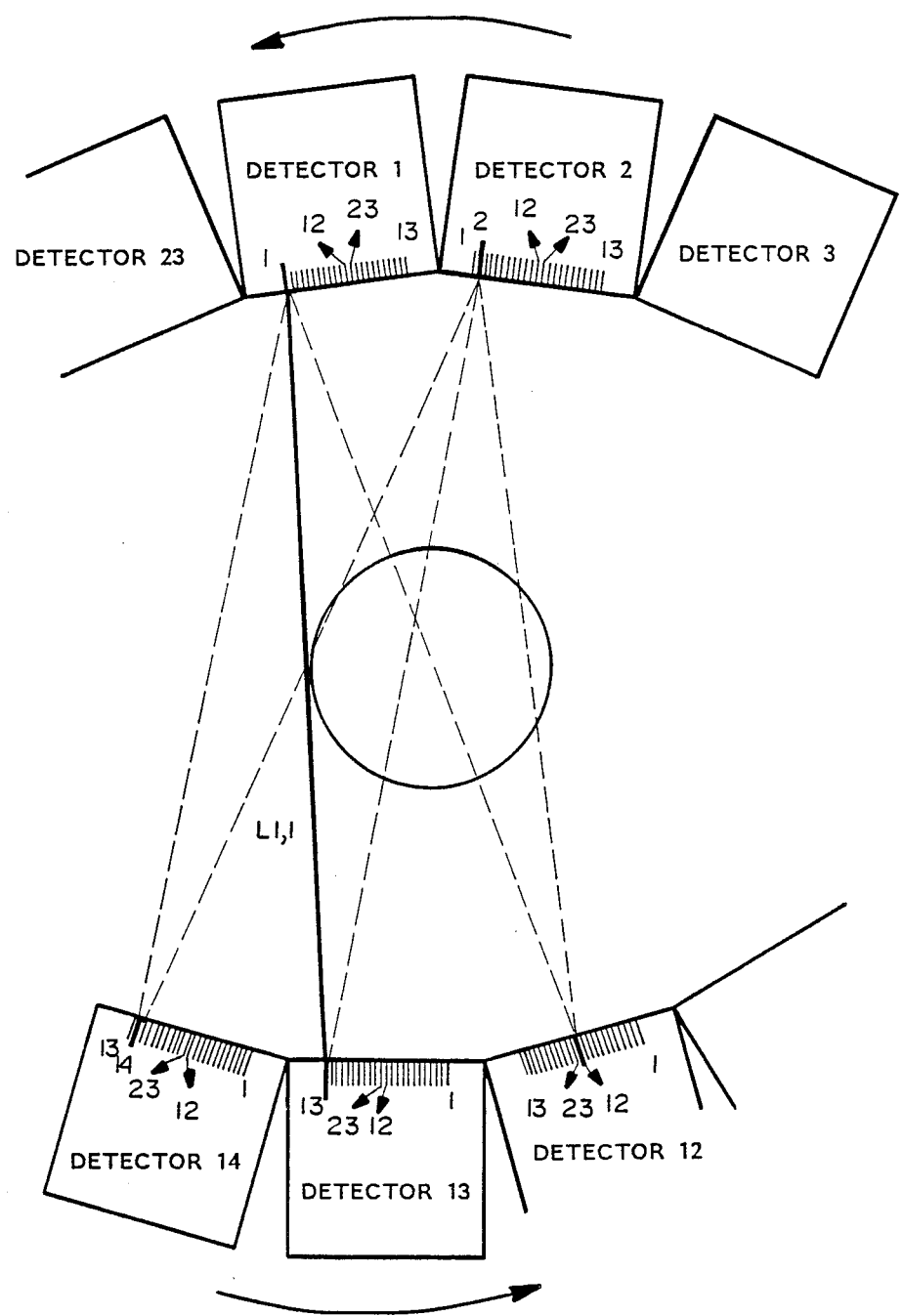
FIGS. 11-14 illustrate in detail an exemplary rebinning of selected single coincident lines of projection image data.
Figure 12:
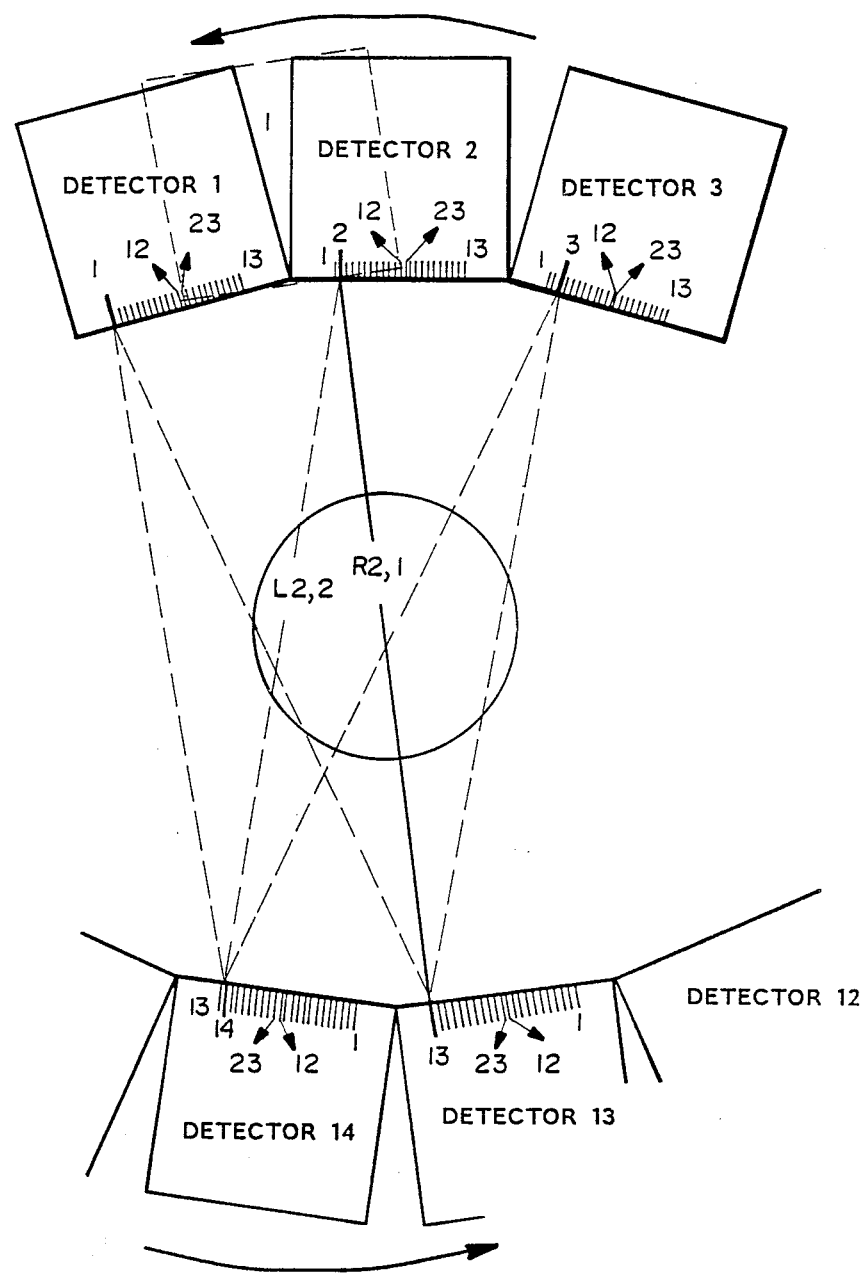
Figure 13:
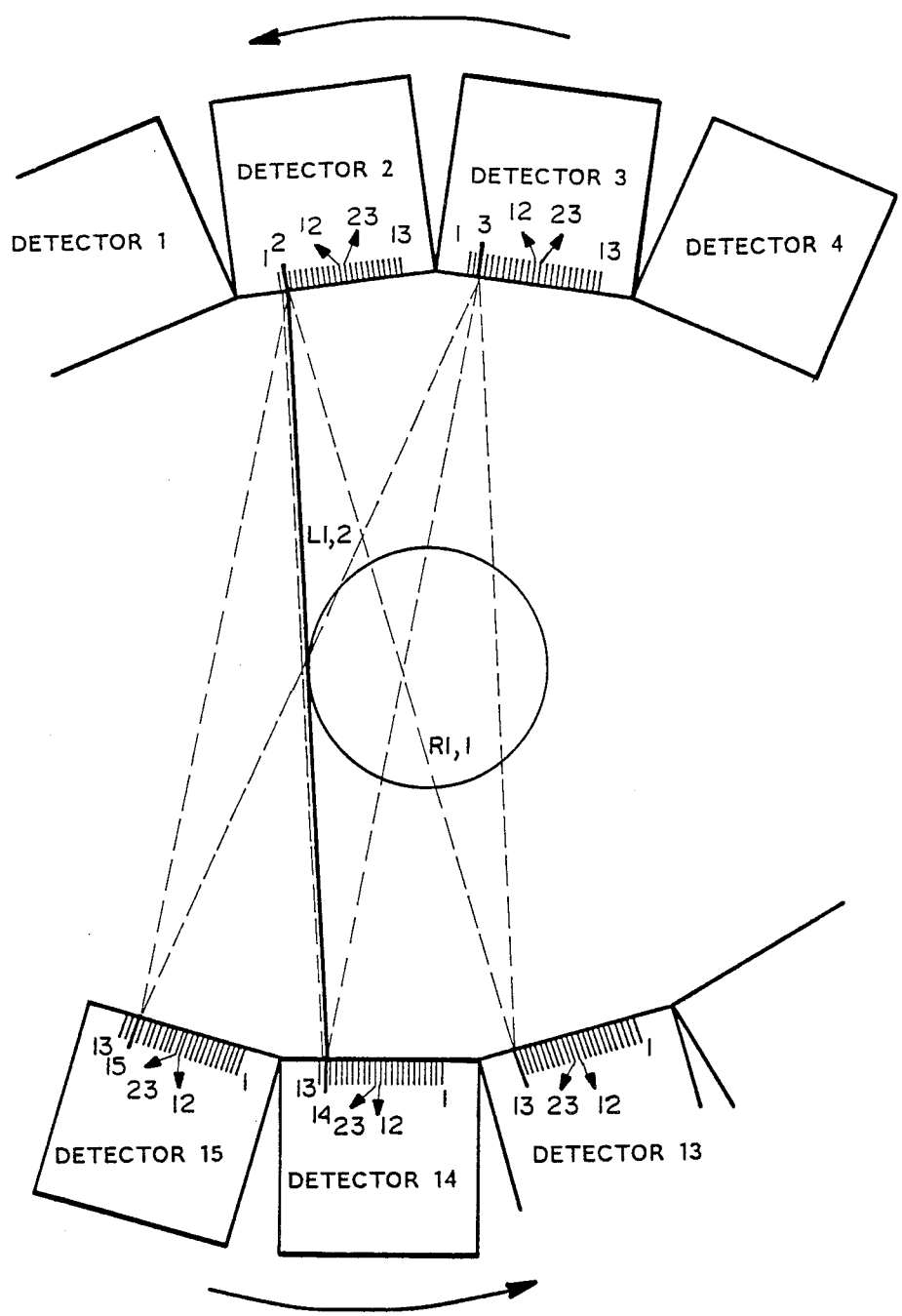
Figure 14:
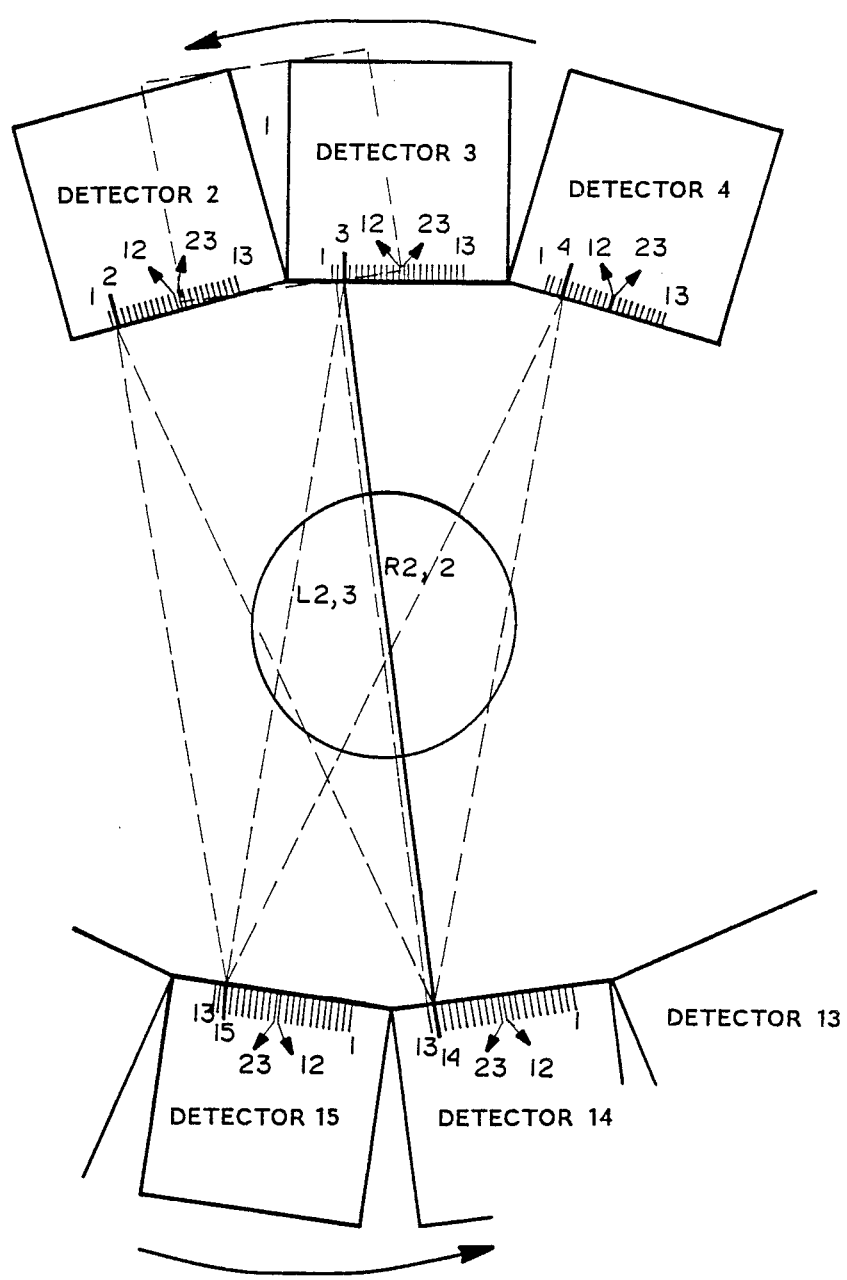

FIG. 10 depicts a simulated image that might be obtained with the exemplary FIG. 3 embodiment by taking sufficiently fine view angles as to produce projection image data over 92 successive view angles, each set having 128 parallel equally spaced-apart ray members. This image is of a Hoffman resolution phantom having included therewithin circular resolution areas of diameters 2, 4, 6, 8 millimeters with respect to separations of 2, 4, 6, and 8 millimeters. As can be seen from an original photograph of this simulated image, the expected approximately 2 millimeter resolution has been obtained.

In our exemplary Mini-Brain PET embodiment, the size of the system diameter is dictated by the size of the object to be imaged, i.e.,, in this case the human brain. The sensitivity of the system is proportional to the solid angle of the detector area, and inversely proportional to the square of the system diameter. For this example, we have chosen system diameter of 20 cm to 35 cm.

The next important parameter we choose for our example was the detector size, i.e., we wanted a reasonably large and high speed scintillation detector with reasonably high Z (atomic number). For this we have chosen $BaF_2$ which currently appears as an optimal choice. $BaF_2$ being Z = 52, with size of 2"×2" will provide near 100% detector efficiency for 511 KeV photons with time resolution as good as 200-400 ps FWHM. This will provide excellent random rejection capability and even time-of-flight imaging capability.

The number of detectors is chosen in our example to be an odd number to better obtain the fine sampling required for the high resolution imaging. Thus, we chose the number of total detectors to be 17, 19, 21 or 23 with size of 2"×2" for the Mini-Brain PET system example, with 23 detectors being preferable.

The aperture size and number of detector aperture offset points for our example were then determined by the image volume in which we were interested. For this we set a 5 cm diameter image volume of area. In this case, each detector makes a coincident line with two opposite detectors. With an odd number of detectors employed and the above two combinations, then, the aperture offset is determined and for which this example is 1.17 mm. The latter also satisfies the Nyquist sampling rate for the resolution in which we are initially interested, i.e., 2-3 mm FWHM. The positions of the shadow opening are located within some margin from the edge of the detector to ensure the detection efficiency for the incoming 511 Kev annihilation photons.

An exemplary spacing with 23 detectors is given with which a substantially equally spaced substantially parallel ray set, after rebinning, can be obtained and used for projection image data. Aperture center of the offset can be calculated as (from the center of the detector face):

center of offset for detectors 1 to 12, = −13 mm + (i−1)1.17 mm (i=1 to 12) center of offset for detectors 13 to 23 12 mm − (i−13)1.17 mm (i=13 to 23)

The margin from the edge of the detector to the aperture center is preferably larger than 12 mm, to ensure minimum loss of detector efficiency.

After completion of data acquisition at 46 gantry positions and rebinning, one obtains 46 coincidence lines per each view for 23 views. However, among the 46 lines in each view, two lines which are not substantially parallel and/or equally spaced to other rays are discarded. The number of coincidence lines that form a single view of projection image data is, therefore, 44 parallel rays in this example.

The rebinning procedure in the example of our Mini-Brain-PET system embodiment is accomplished by using pre-assigned lookup tables. As the gantry is rotated to pre-assigned angular positions, the coincidence data are acquired. The coincidence data are, then, sorted into "bins" and later combined to form view sets of parallel projection image data. For the center 5 cm diameter imaging volume, a total of 23 coincidence data are obtained at each gantry position. (The number of gantry positions can be made even multiples of the number of detectors e.g., detectors 46 or 92.) Those 23 coincidence lines are then sorted into proper "bins" according to the lookup table. After data acquisition at each gantry position, data are accumulated into the 46 bins. After completion of data collection on all 46 positions (or multiples of 46 positions), substantially parallel ray projection data sets for 23 views (or multiples of 23 views) are obtained. An overall rebinning flow diagram is shown in FIG. 11-14. The coincidence lines for outside 5 cm area are also obtained and can be rebinned in a similar procedure as should now be apparent.

Figure 16A:
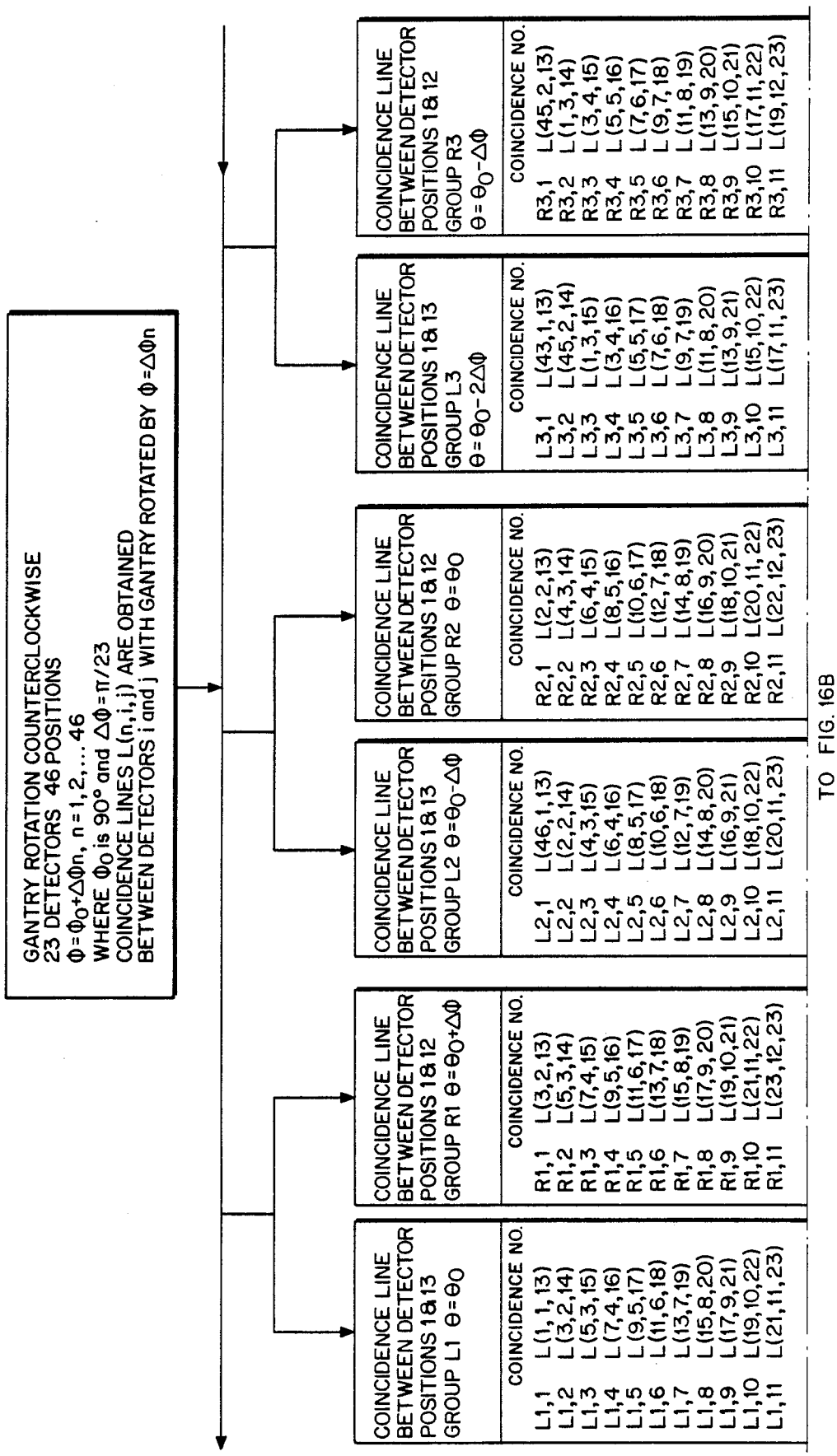
Figure 16B:
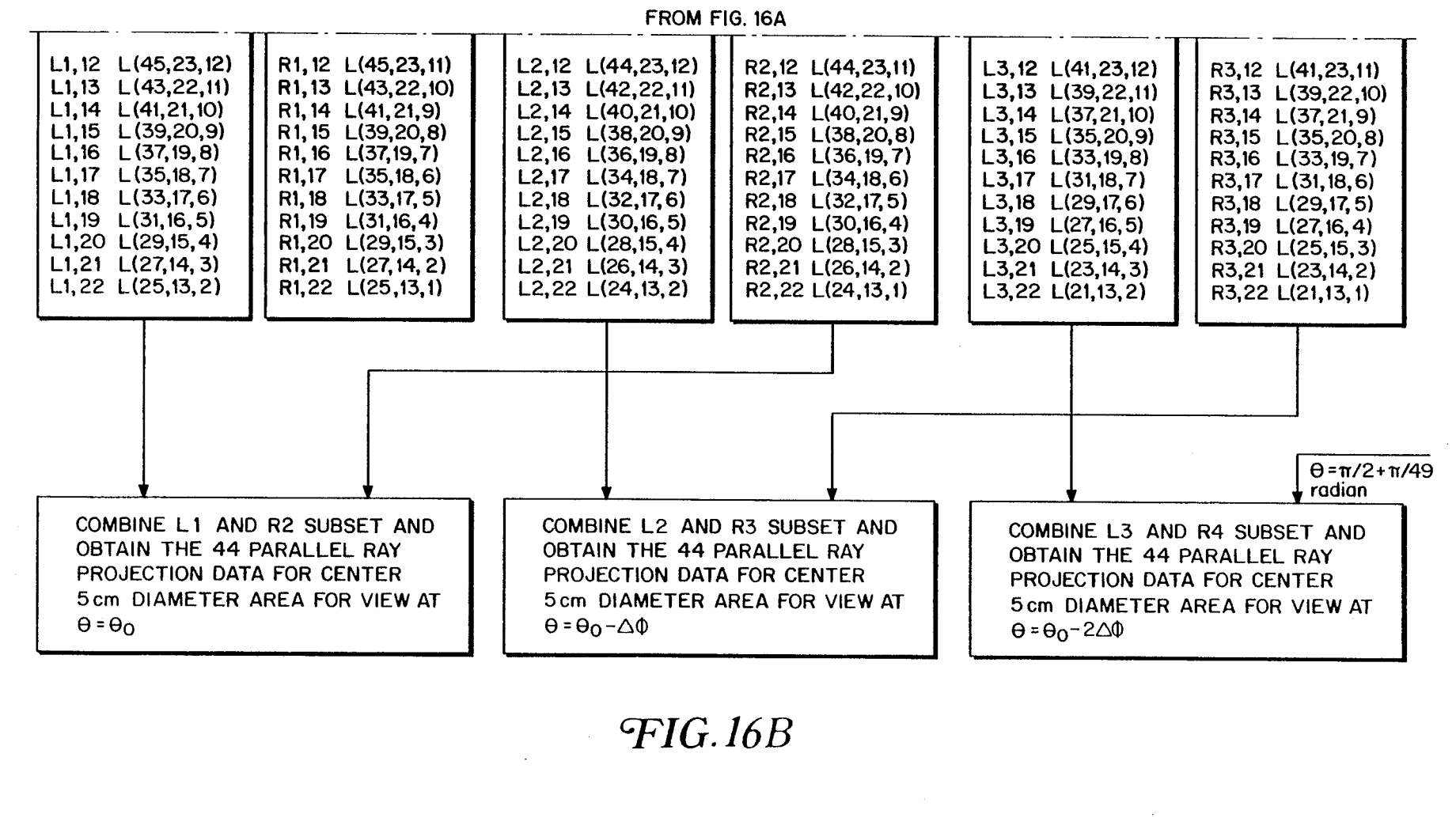

A "bin" is the storage location for a group of sorted coincidence line data from the data sets originally obtained at different gantry positions. An example of the bin group for the first four gantry positions is shown in FIGS. 15A, 15B. As an example, bin L1 and R2 with coincidence lines fully accumulated therein is illustrated in FIGS. 16A, 16B and corresponding coincidence lines at the gantry position 1 to 4 are shown in FIGS. 11-14. Some exemplary bin combinations are shown in FIGS. 16A, 16B where the projection data for view i.e., $\theta=\phi_o, \theta=\phi_o-\pi/23$ and $\theta=\theta_o-2\pi/23$ are shown. Note that $\theta_o=\phi_o+\pi/46$ radian with $\phi_o=90°$, corresponds to the y-axis.

An exemplary rebinning procedure is illustrated for one representative view of the projection data, i.e., for a view with angle $\theta=\phi_o+\pi/46$ radian or $\theta=\theta_o$. The left half of the projection data L1 group is obtained by accumulation of the coincidence lines between initial positions of detectors 1 and 13 with gantry positions $\phi=\phi_o+(2n-1)\pi/23$ radian where n=1,2...,23.

Figure 18:
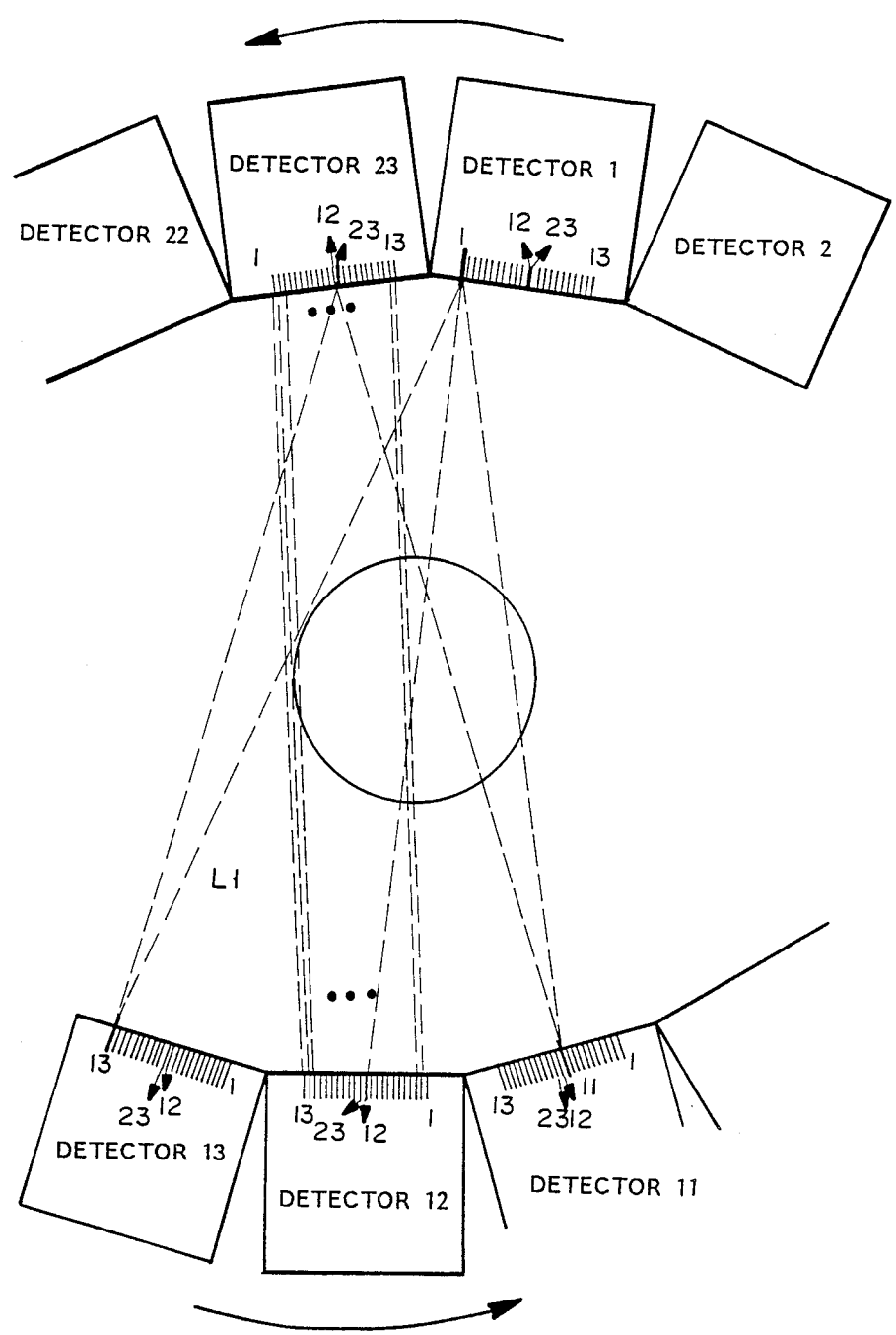
FIGS. 18-20 depict rebinning of a complete set of substantially parallel lines of data.

An illustration of the accumulation of rebinned coincidence lines for the L1 group is shown in FIG. 18. The right half of the projection data R2 group is also obtained similarly by accumulation of the coincidence lines between the initial positions of detectors 1 and 12 with gantry positions $\phi=\phi_o+2n\pi/23$ radian where n=1,2,... 22.

Figure 19:
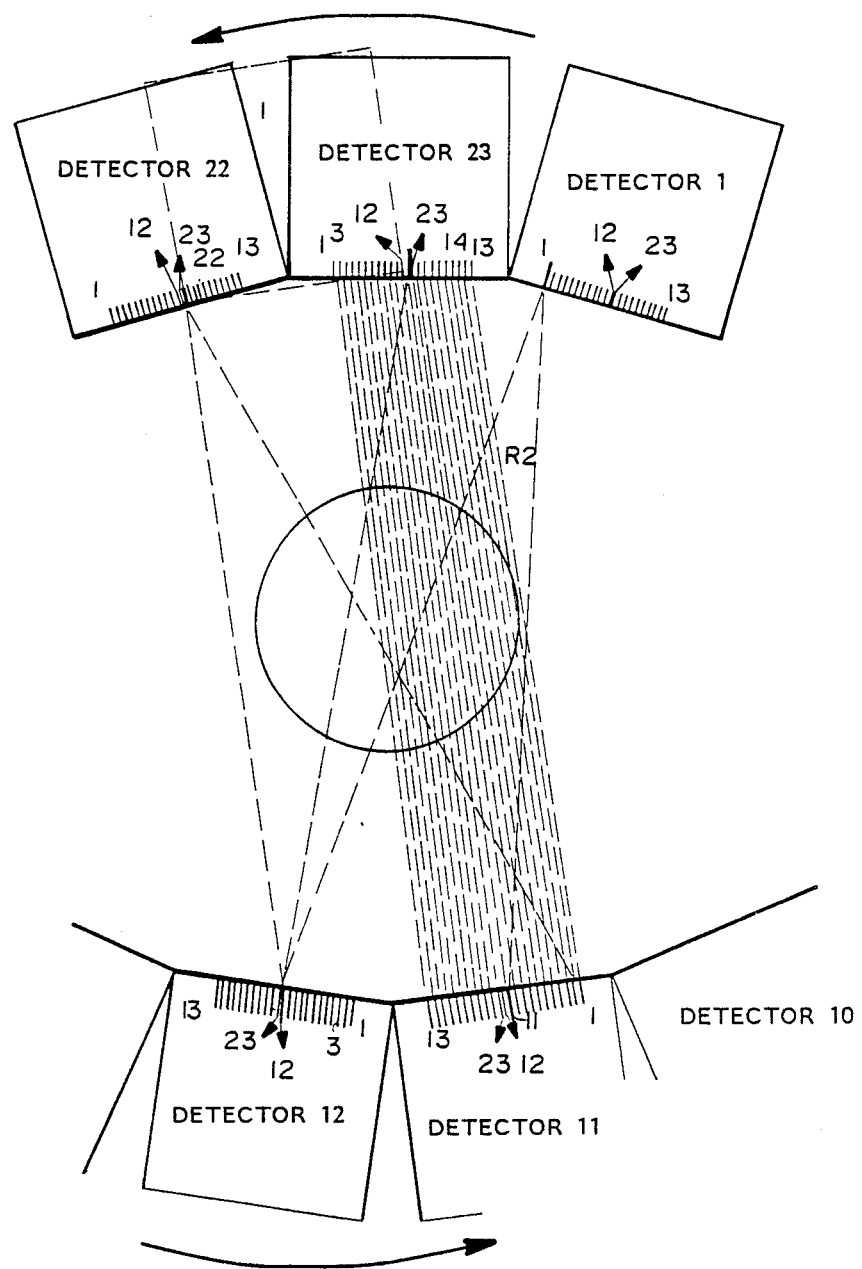
Figure 20:
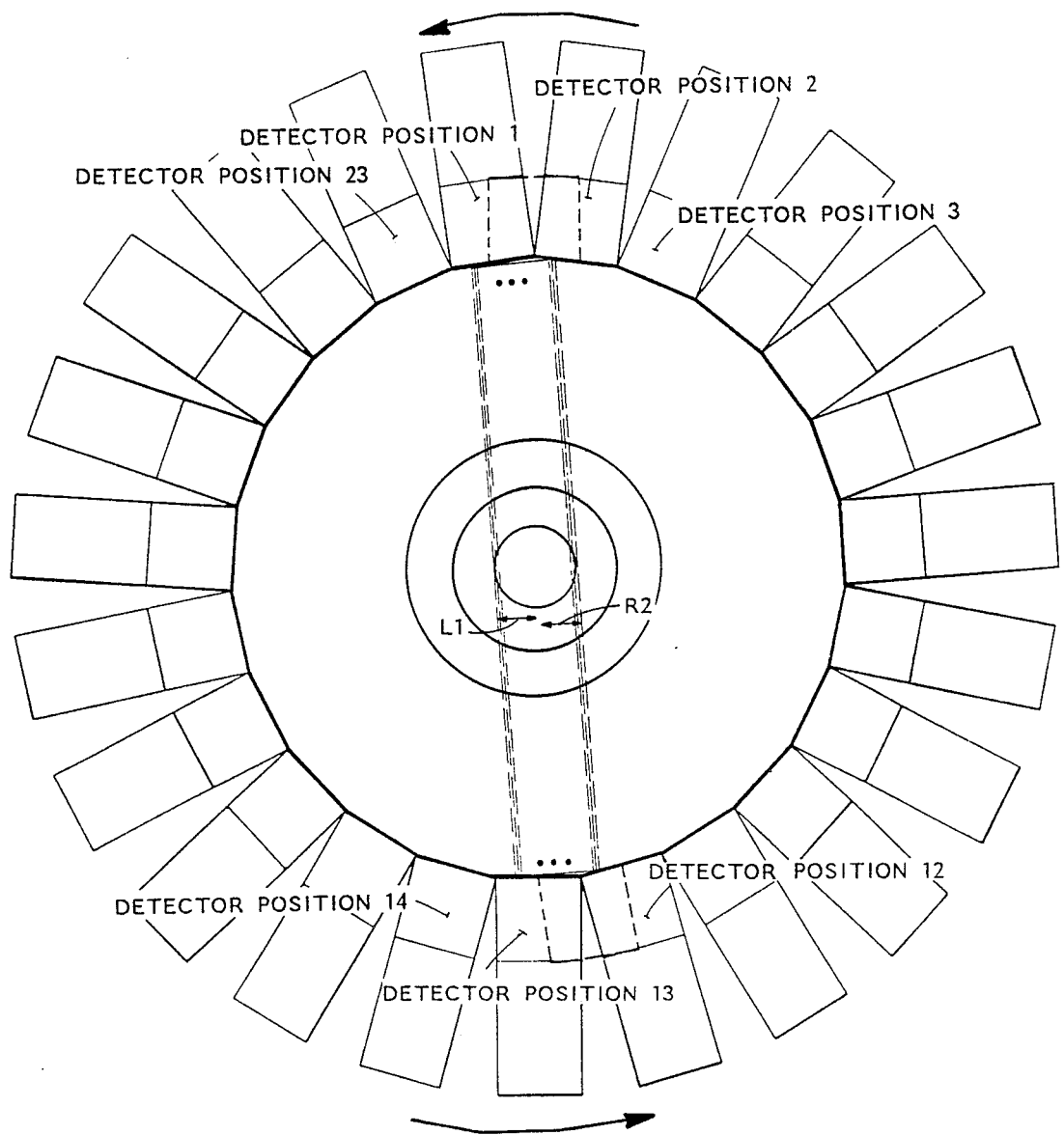

An illustration of the rebinned coincidence lines accumulation for R2 is also shown in FIG. 19. Projection data for other views are accumulated in the same fashion but with different orders as the gantry is rotated. Final projection data at $\theta_o$ is then formed by combining the L1 with R2 groups and is also the first view projection data. This final projection data formation is depicted at FIG. 20 for L1 and R2.

Figure 17:
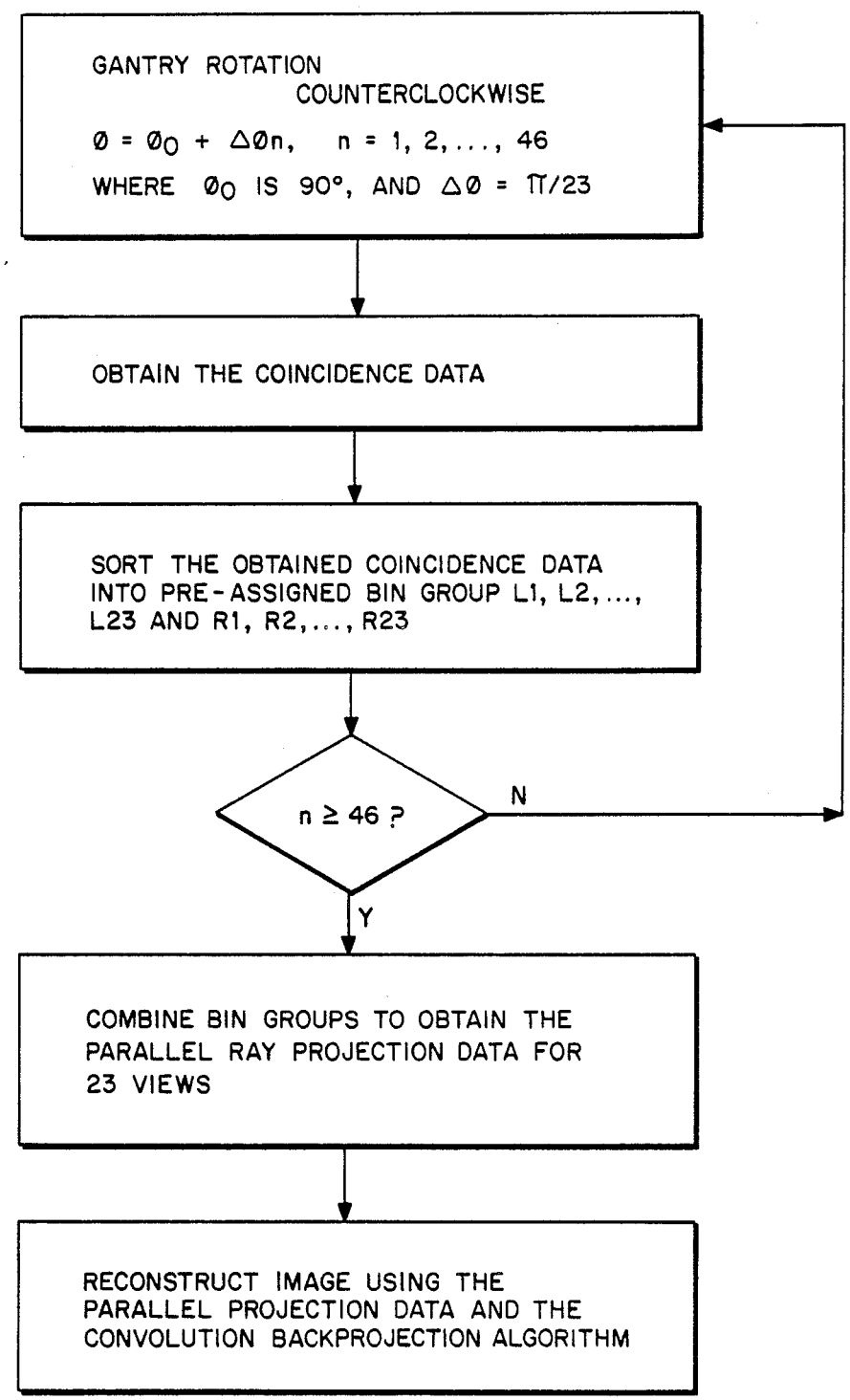

One general algorithm for rebinning is depicted in the flow diagram of FIG. 17 and may be programmed for computerized implementation as will be apparent.

Figure 21A:
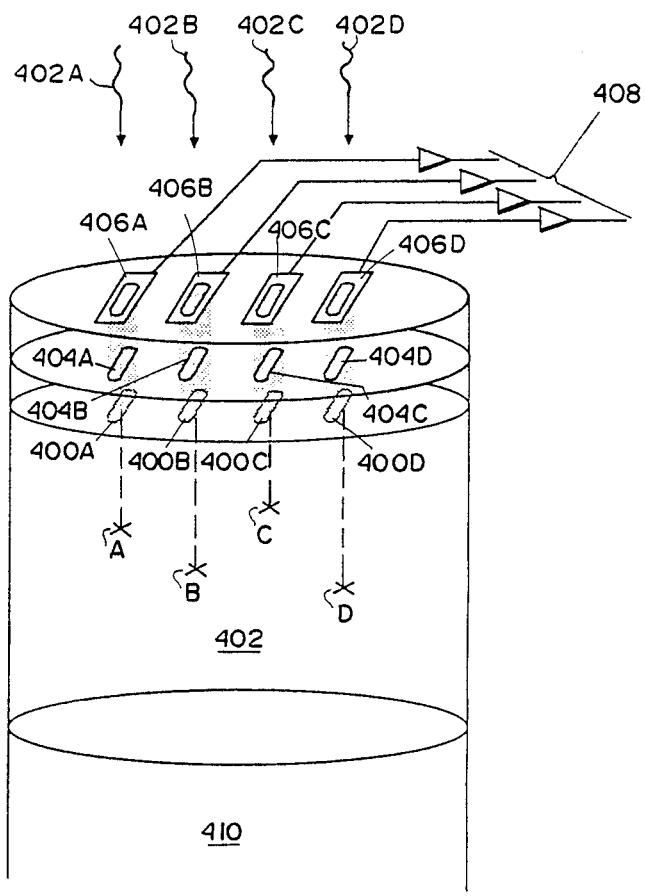
FIGS. 21A, 21B and 22 depict an alternate further exemplary embodiment using multiple collimator apertures to provide increased sensitivity.
Figure 21B:
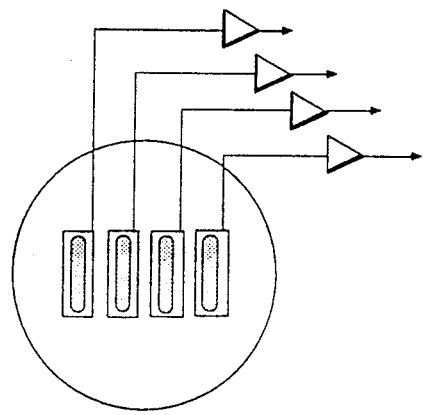
Figure 22:
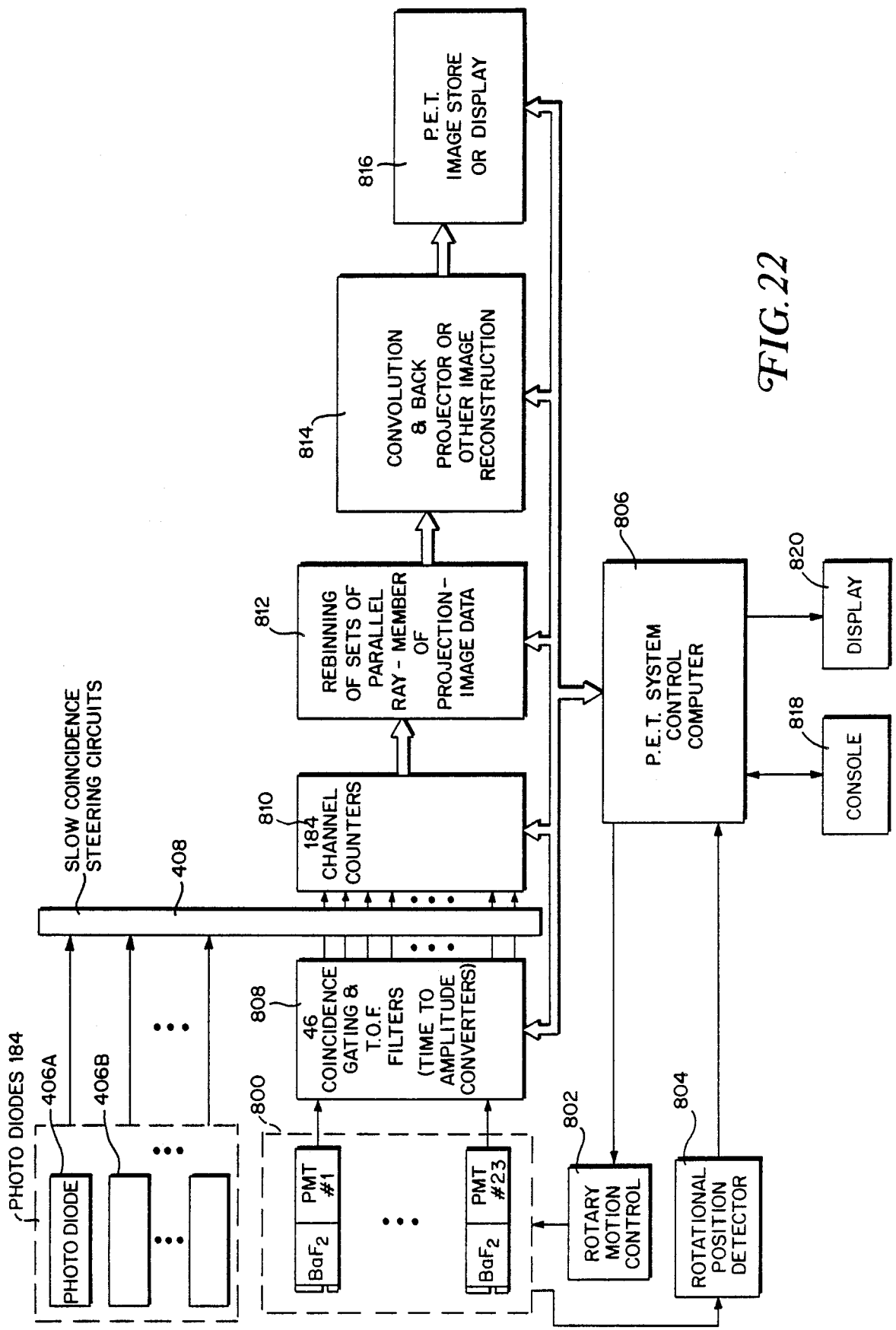

FIGS. 21A, 21B and 22 illustrate an alternative embodiment using multiple collimator apertures 400A, 400B, 400C and 400C (e.g., four) per detector crystal 402. In this example, use of four apertures allows one to identify interaction points A, B, C, D for four respectively associated photons 402A, 402B, 402C, 402D incident on the detector 402 surface. Thin parallel plates (cumulatively providing a collimator thickness of about 1 cm in this example where N=4 and the crystal diameter is about 5 cm) are used to form aligned optical apertures 404A, 404B, 404C, 404D (i.e., of material opaque to scintillation photons back-directed from crystal 402). Such optical collimator apertures will permit identification of the position of interaction points A, B, C, D of the 511 Kev photons incident on the crystal 402.

Signals obtained from each photodiode (i.e., 406A, 406B, 406C, 406D (i.e., from scintillation photons generated in crystal 402 at sites A, B, C, D, respectively, by incident annihilation photons 402A, 402B, 402C, 402D which pass unimpeded through the silicon photodiodes and the optical collimator) are fed to slow coincidence steering circuits 408 for routing the fast coincidence signals obtained from the PMT 410.

The number of optical collimator apertures/photodiodes, etc., can be extended to thereby increase the coincidence counting albeit with less position identification capability. It also should be noted that the set of plural apertures should be progressively offset by different amounts from one detector to the next (as described above for the single aperture embodiments) to obtain rebinned sets of substantially parallel projection image data for use in image reconstruction.

The block diagram of FIG. 22 uses many of the same components as the FIG. 8 embodiment and its operation is believed self-evident to those skilled in the art in view of the above description. The increased number of channel counters (to which inputs are steered by the slow coincidence circuits 408 as a function of photodiode array outputs) is depicted.

Although the exemplary embodiments have been described as a single ring device, those skilled in the art will recognize that by mere replication (and suitable further conventional signal processing) it can be extended in the axial direction to any desired number of ring arrays (thus providing three dimensional imaging capability). Three dimensional PET imaging can thus be provided as will be apparent to those in the art. Furthermore, although the preferred exemplary embodiment utilizes a one-to-one correspondence between scintillator crystals and photo-multiplier tubes, Anger-type position discrimination may be utilized so as to utilize an array of N PMTs within array of a different (larger) number M of scintillation detector crystals.

While only a few exemplary embodiments have been described in detail, those skilled in the art will recognize that many variations and modifications may be made in these exemplary embodiments while yet retaining many of the novel features and advantages of this invention. Accordingly, all such variations and modifications are intended to be included within the scope of the appended claims.

What is claimed is:

1. A positron emission tomography (PET) system comprising:
    a ring array of collimated gamma ray detectors, each detector being substantially larger in a circumferential array dimension than the image resolution of the system,
    said ring array being mounted for rotation about an image volume, and
    each detector having at least one collimation aperture located at a relative position on the detector which is a function of detector location within the ring array.

2. A positron emission tomography system as in claim 1 wherein said ring array is mounted for incremental rotation between predetermined view angle positions at each of which positions the detectors remain fixed while acquiring PET image data thereat.

3. A positron emission tomography system as in claim 2 further comprising:
    rebinning means for re-grouping the members of image data sets acquired from the detectors in corresponding ones of said positions into rebinned image data sets each of which rebinned set includes projection image data for a plurality of substantially equally spaced-apart substantially parallel ray lines through an image volume.

4. A positron emission tomography system as in claim 1 including time-of-flight filtering means for discriminating against positron emission data emanating from outside a desired portion of an image volume viewed by said detector array.

5. A positron emission tomography system as in claim 1 wherein:
    a first sequentially located approximately half of said ring array of detectors have respective collimator aperture offsets which progressively change in one sense with respect to the detector center as a function of detector location; and
    the remaining sequentially located approximately half of said ring array of detectors have respective collimator aperture offsets which progressively change in a second sense, opposite to said first sense, with respect to the detector center as a function of detector location.

6. A position emission tomography system as in claim 1 wherein each gamma ray detector collimator has plural apertures.

7. A positron emission tomography (PET) system comprising:
    a rotationally mounted ring array of collimated gamma ray detection scintillation crystals, each crystal being individually coupled to a photo-multiplier tube and said ring array being disposed circumferentially about a predetermined image volume of diameter D;
    each of said detector crystals having a cylindrical form with diameter of approximately D.

8. A positron emission tomography system as in claim 7 wherein each scintillation crystal is affixed to a collimator having an aperture located at a predetermined position on the crystal which is different from the aperture location on other detector crystals.

9. A positron emission tomography system as in claim 7 wherein said ring array of detectors is mounted for incremental rotational movement between fixed positions throughout approximately 360° of rotation with respect to said image volume.

10. A positron emission tomography system as in claim 7 wherein each detector comprises a collimator having an aperture located at a predetermined position which is different from the aperture location on other detectors by an integer multiple of a predetermined ray spacing dimension representing a predetermined spacing between ray lines of a substantially parallel ray projection image data set to be acquired from said detectors.

11. A positron emission tomography (PET) system comprising:
   a rotatable ring array of N circumferentially spaced collimator elements disposed about a PET image volume and shielding a further outer ring of N gamma ray detectors except through a plurality of collimator apertures,
   said collimator apertures being located to define predetermined projection rays for gamma ray detection at each of plural view positions of said rotatable ring including plural sets of substantially uniformly distributed substantially parallel ray projection PET image data.

12. A positron emission tomography system as in claim 11 wherein said gamma ray detector ring includes a separate gamma ray detector scintillator crystal optically coupled to a photo-multiplier tube and affixed to each of said collimator elements for common rotation therewith.

13. A positron emission tomography system as in claim 11 wherein the aperture of each said collimator element is located at a predetermined position with respect to a corresponding detector which portion is offset from the aperture position for other detectors.

14. A positron emission tomography system as in claim 11 wherein said aperture locations are positioned to produce first sets of projection PET imaging data capable of being subsequently rebinned to produce second sets of projection PET imaging data in which each second set includes a plurality of substantially equally spaced-apart substantially parallel projection rays at a common viewing angle through an image volume.

15. A positron emission tomography system as in claim 11 wherein said detectors each have an array dimension of D and said uniformly distributed projection PET image data is substantially uniformly distributed through a predetermined image volume of diameter at least approximately equal to D.

16. A positron emission tomography system as in claim 15 wherein the aperture of each collimator aperture is offset with respect to an associated detector relative to other collimator apertures by an integer multiple of a predetermined dimension R.

17. A positron emission tomography system as in claim 16 including means for rebinning PET image data obtained from said detector ring to produce sets of substantially projection PET image data each set having a plurality of substantially parallel projection rays spaced-apart by dimension R.

18. A computed tomographic imaging system comprising:
   a ring array of photon detectors distributed circumferentially about an image volume,
   each photon detector having a collimator with an aperture that is offset from the center of its associated detector by a predetermined dimension different from other detectors so as to cause a plurality of opposingly situated detectors to view oppositely directed photons produced by emissions of a radionuclide within the image volume along projected ray lines which are offset from the center of said image volume;
   means for rotating said ring of detectors and the associated collimators with respect to said image volume through a succession of view angles to produce plural sets of projection image data.

19. A system as in claim 18 wherein said means for rotating holds the detectors in a fixed view angle position while emission data is accumulated before incrementally changing the rotational position to each new view angle position at which the detector location is again temporarily fixed while image data is acquired.

20. A system as in claim 19 further comprising:
   means for rebinning the image data sets successively acquired at each view angle to produce rebinned image data sets, each such rebinned set comprising a plurality of spaced-apart substantially parallel projection rays through said image volume at a predetermined view angle with respect to the image volume.

21. A system as in claim 20 wherein each photon detector comprises a $BaF_2$ scintillator crystal optically coupled to a photo-multiplier tube which provides electrical pulse outputs indicative of photons incident on the scintillator crystal through its associated collimator aperture, and said system further comprising:
   electrical pulse processing circuits for detecting substantially coincident pulses emanating from opposingly situated detectors and including time-of-flight electrical timing circuits for filtering out detected coincidences unless emanating from a desired portion of the image volume;
   means for counting thus filtered outputs from said pulse processing circuits to acquire first sets of image data representing the number of emissions occurring within the desired image volume along projection ray lines between opposingly situated ones of the detectors;
   means for rebinning individual members of said first sets of image data into second sets of image data, each of said second sets comprising data members representing positron emissions occurring along a plurality of substantially equally spaced-apart substantially parallel projection ray lines through said image volume at a predetermined view angle with respect to the image volume.

22. A system as in claim 18 wherein there are 23 of said detectors, each being approximately 5 cm in dimension disposed about the inside circumference of a rotatable ring-shaped gantry.

23. A system as in claim 22 wherein each collimator has an approximately 4 mm aperture in the circumferential array direction which is offset from the center of each successive detector by $$-X+(i-1)R \text{ mm } (i=1 \text{ to } 12 \text{ for detectors } 1 \text{ to } 12),$$

$$Y-(i-13)R \text{ mm } (i=13 \text{ to } 23 \text{ for detectors } 13 \text{ to } 23)$$

where X and Y define the maximum aperture offsets in opposing directions, when R is the ray spacing between projection data samples and where the detector numbers are sequentially assigned to correspondingly sequentially located detectors around the ring array circumference.

24. A system as in claim 18 wherein said means for rotating provides an approximately 360° of rotation for said detectors.

25. A system as in claim 18 wherein said means for rotating provides substantially more than 90° of rotation for said detectors.

26. A system as in claim 18 wherein each collimator has plural apertures, each such aperture being associated with a photo-electric transducer connected to slow coincidence circuits used to steer the outputs of faster coincidence circuits connected to the detectors thereby locating the position of an incident coincidence photon with respect to an individual one of said plural apertures.

27. A computed tomographic imaging system comprising:
   a rotatably mounted ring array of N gamma ray detectors disposed about an image volume;
   each said detector having a scintillation crystal with a gamma-ray collimator having a plurality M of apertures spaced-apart in a circumferential dimension; and
   the group of M apertures on each crystal being located at a different relative position with respect to the crystal than the location groups associated with other N-1 crystals.

28. A system as in claim 27 further comprising:
   an optical collimator disposed on each detector in addition to its gamma-ray collimator,
   said optical collimator having a plurality M of optical apertures respectively aligned with the M apertures of the gamma-ray collimator for passing scintillation photons from the crystal therethrough; and
   a first photoelectric transducer disposed in association with each aperture of the optical collimator to intercept scintillation photons passing from the crystal through the respectively associated collimator apertures.

29. A system as in claim 28 further comprising:
   an array of second photoelectric transducers optically coupled directly to said ring array of gamma ray detectors;
   a plurality of p fast-coincidence circuits connected to said array of second photoelectric transducers for providing an electrical pulse when substantially coincident scintillations occur in opposingly disposed scintillation crystals;
   a plurality MP of slow-coincidence circuits connected to said first photoelectric transducers for producing steering signals indicative of which individual one of said M apertures associated with a given crystal has passed the gamma ray photon corresponding to a substantially simultaneous scintillation event in opposingly situated crystals;
   a plurality MP of event counters; and
   steering circuits controlled by said steering signals for accepting a plurality P inputs from said P fast coincidence circuits and for steering a selected one of said inputs to a selected one of said MP event counters.

30. A method for generating projection image data in a positron emission tomography (PET) system, said method comprising the steps of:
   rotating a ring array of collimated gamma-ray detectors about an image volume, each said detector having at least one collimation aperture located thereon in a position different from the location of a similar aperture on other detectors;
   acquiring coincidence position emission data at each of plural rotational positions of the ring array; and
   rebinning said data into sets of substantially equally-spaced substantially parallel rays of PET projection image data.

31. A method as in claim 30 wherein said rotating step includes incremental rotation of said ring array between predetermined view angle positions at each of which positions the detectors remain fixed while acquiring PET image data thereat.

32. A method as in claim 30 including the step of discriminating against positron emission data emanating from outside a desired portion of an image volume viewed by said detector array.

33. A method as in claim 30 wherein each gamma ray detector collimator has plural apertures.

34. A positron emission tomography (PET) method comprising:
   rotating a ring array of collimated gamma ray detection scintillation crystals, each crystal being individually coupled to a photo-multiplier tube and said ring array being disposed circumferentially about a predetermined image volume of diameter D;
   each of said detector crystals having a cylindrical form with diameter of approximately D; and
   acquiring projection image data at successive view angles during said rotation.

35. A positron emission tomography method as in claim 34 wherein each scintillation crystal is affixed to a collimator having an aperture located at a predetermined position on the crystal which is different from the aperture location on other detector crystals.

36. A positron emission tomography method as in claim 34 wherein said ring array of detectors is incrementally rotated between fixed positions throughout approximately 360° of rotation with respect to said image volume.

37. A positron emission tomography method as in claim 34 wherein each detector includes a collimator having an aperture located at a predetermined position which is different from the aperture location on other detectors by an integer multiple of a predetermined ray spacing representing a predetermined spacing between ray lines of a substantially parallel ray projection image data set to be acquired from said detectors.

38. A positron emission tomography (PET) method comprising:
   rotating a ring array of N circumferentially spaced collimator elements disposed about a PET image volume and shielding a further outer ring of N gamma ray detectors except through a plurality of collimator apertures,
   said collimator apertures being located to define predetermined projection rays for gamma ray detection at each of plural view positions of said rotatable ring including plural sets of substantially uniformly distributed substantially parallel ray projection PET image data; and
   acquiring said image data during substantially 360° rotation of said ring array.

39. A positron emission tomography method as in claim 38 wherein said gamma ray detector ring includes a separate gamma ray detector scintillator crystal optically coupled to a photo-multiplier tube and affixed to each of said collimator elements for common rotation therewith.

40. A positron emission tomography method as in claim 38 wherein the aperture of each said collimator element is located at a predetermined position with respect to a corresponding detector which portion is offset from the aperture position for other detectors.

41. A positron emission tomography method as in claim 38 wherein said aperture locations are positioned to produce first sets of projection PET imaging data capable of being subsequently rebinned to produce second sets of projection PET imaging data in which each second set includes a plurality of substantially equally spaced-apart substantially parallel projection rays at a common viewing angle through an image volume.

* * * * *